US010470886B2

(12) United States Patent
Bake et al.

(10) Patent No.: US 10,470,886 B2
(45) Date of Patent: Nov. 12, 2019

(54) METHOD OF A RIG

(71) Applicant: EPISURF IP-MANAGEMENT AB, Stockholm (SE)

(72) Inventors: Nina Bake, Lidingö (SE); Richard Lilliestråle, Stockholm (SE)

(73) Assignee: EPISURF IP-MANAGEMENT AB, Stockholm (SE)

( * ) Notice: Subject to any disclaimer, the term of this patent is extended or adjusted under 35 U.S.C. 154(b) by 276 days.

(21) Appl. No.: 15/324,437

(22) PCT Filed: Jul. 9, 2015

(86) PCT No.: PCT/EP2015/065780
§ 371 (c)(1),
(2) Date: Jan. 6, 2017

(87) PCT Pub. No.: WO2016/005541
PCT Pub. Date: Jan. 14, 2016

(65) Prior Publication Data
US 2017/0156890 A1 Jun. 8, 2017

(30) Foreign Application Priority Data
Jul. 9, 2014 (WO) ................ PCT/EP2014/064760

(51) Int. Cl.
*A61F 2/30* (2006.01)
*A61B 17/15* (2006.01)
(Continued)

(52) U.S. Cl.
CPC ................ *A61F 2/30* (2013.01); *A61B 17/15* (2013.01); *A61B 17/154* (2013.01); *A61B 17/17* (2013.01);
(Continued)

(58) Field of Classification Search
CPC .............. A61B 34/10; A61B 2034/101; A61B 2034/102; A61B 2034/105;
(Continued)

(56) References Cited

U.S. PATENT DOCUMENTS 4,180,910 A   1/1980   Straumann et al.
4,197,645 A   4/1980   Scheicher
(Continued)

FOREIGN PATENT DOCUMENTS

CN   102083374 A   6/2011
EP   1 698 307 A1   9/2006
(Continued)

OTHER PUBLICATIONS

Notification of Reasons for Refusal dated Mar. 29, 2018 issued in corresponding Japanese patent application No. 2017-500881 (4 pages) and English-language translation thereof (5 pages).
(Continued)

*Primary Examiner* — Matthew J Lawson
(74) *Attorney, Agent, or Firm* — Drinker Biddle & Reath LLP

(57) ABSTRACT

A method for designing and making a rig that includes a hollow tubular shell, and the interior of said shell defines at least first and second intersecting cylinders. The method includes identifying a damage area, presenting a 3D view of identified damage area, generating a 3D model of a virtual rig, and producing a rig according to the virtually created rig. The generating includes virtually placing in 3D view a shape covering or partly covering damage area, and creating, based on the position of the virtually placed shape, a position of hollow tubular rig shell of the virtual rig; and selecting the at least first and second intersecting cylinders of the virtual rig, based on the size and form of the virtually placed shape, and creating a positioning surface of the virtual rig which is
(Continued)

a bone and/or cartilage-engaging end of hollow tubular shell.

17 Claims, 14 Drawing Sheets

(51) Int. Cl.
    *A61B 17/17*     (2006.01)
    *A61B 34/10*     (2016.01)
    *A61F 2/36*     (2006.01)
    *A61F 2/38*     (2006.01)
    *A61F 2/46*     (2006.01)

(52) U.S. Cl.
    CPC .......... *A61B 17/1767* (2013.01); *A61B 34/10* (2016.02); *A61F 2/30756* (2013.01); *A61F 2/36* (2013.01); *A61F 2/38* (2013.01); *A61F 2/4657* (2013.01); *A61B 2034/108* (2016.02); *A61F 2002/3013* (2013.01); *A61F 2002/30331* (2013.01); *A61F 2002/30878* (2013.01); *A61F 2002/30891* (2013.01); *A61F 2002/30892* (2013.01); *A61F 2002/30897* (2013.01)

(58) Field of Classification Search
    CPC ............ A61B 2034/108; A61B 17/155; A61B 17/1757; A61B 2/461; A61B 17/1764; A61B 17/1767; A61F 2/4618; A61F 2002/30764; A61F 2/30756
    See application file for complete search history.

(56) References Cited

U.S. PATENT DOCUMENTS

| | | | |
|---|---|---|---|
| 4,964,865 A | 10/1990 | Burkhead et al. | |
| 5,520,692 A | 5/1996 | Ferrante | |
| 5,716,360 A | 2/1998 | Baldwin et al. | |
| 5,743,916 A | 4/1998 | Greenberg et al. | |
| 5,976,147 A | 11/1999 | LaSalle et al. | |
| 6,063,091 A | 5/2000 | Lombardo et al. | |
| 6,165,177 A | 12/2000 | Wilson et al. | |
| 6,251,143 B1 | 6/2001 | Schwartz et al. | |
| 6,306,142 B1 | 10/2001 | Johanson et al. | |
| 6,520,964 B2 | 2/2003 | Tallarida et al. | |
| 6,799,066 B2 | 9/2004 | Steines et al. | |
| 7,658,879 B2 | 2/2010 | Solar | |
| 7,713,305 B2 | 5/2010 | Ek | |
| 7,824,181 B2 | 11/2010 | Sers | |
| 7,867,234 B2 | 1/2011 | Collazo | |
| 7,981,122 B2 | 7/2011 | Labadie et al. | |
| 8,062,302 B2 | 11/2011 | Lang et al. | |
| 8,066,708 B2 | 11/2011 | Lang et al. | |
| 8,083,745 B2 | 12/2011 | Lang et al. | |
| 8,105,330 B2 | 1/2012 | Fitz et al. | |
| 8,460,304 B2 | 6/2013 | Fitz et al. | |
| 8,641,721 B2 | 2/2014 | Aram et al. | |
| 8,882,818 B1 | 11/2014 | Vestgaarden | |
| 8,945,135 B2* | 2/2015 | Ries ..................... | A61F 2/3877 606/96 |
| 9,009,012 B2 | 4/2015 | Bake et al. | |
| 9,216,089 B2 | 12/2015 | Major et al. | |
| 9,254,196 B2 | 2/2016 | Bake et al. | |
| 9,386,999 B2 | 7/2016 | Robertson et al. | |
| 9,826,993 B2 | 11/2017 | Bake et al. | |
| 2002/0095214 A1 | 7/2002 | Hyde | |
| 2002/0116006 A1 | 8/2002 | Cohen | |
| 2003/0018337 A1 | 1/2003 | Davis | |
| 2003/0100947 A1 | 5/2003 | Nadler et al. | |
| 2003/0144741 A1 | 7/2003 | King et al. | |
| 2003/0216669 A1 | 11/2003 | Lang et al. | |
| 2004/0098133 A1* | 5/2004 | Carignan ............ | A61B 17/1764 623/20.35 |
| 2004/0147927 A1* | 7/2004 | Tsougarakis ........ | A61F 2/30756 606/53 |
| 2004/0215203 A1 | 10/2004 | Michelson | |
| 2005/0209694 A1 | 9/2005 | Loeb | |
| 2005/0234467 A1 | 10/2005 | Rains | |
| 2006/0198877 A1 | 9/2006 | Steinwachs et al. | |
| 2006/0206208 A1 | 9/2006 | Michelson | |
| 2006/0235539 A1 | 10/2006 | Blunn et al. | |
| 2006/0247790 A1 | 11/2006 | McKay | |
| 2007/0021838 A1 | 1/2007 | Dugas et al. | |
| 2007/0100459 A1 | 5/2007 | Rhodes | |
| 2007/0159487 A1 | 7/2007 | Felt | |
| 2007/0233150 A1 | 10/2007 | Blain et al. | |
| 2007/0276501 A1 | 11/2007 | Betz et al. | |
| 2008/0051793 A1 | 2/2008 | Erickson et al. | |
| 2008/0243127 A1 | 10/2008 | Lang et al. | |
| 2008/0281328 A1 | 11/2008 | Lang et al. | |
| 2009/0209962 A1* | 8/2009 | Jamali ................ | A61B 17/1635 606/81 |
| 2009/0270868 A1 | 10/2009 | Park et al. | |
| 2009/0318927 A1 | 12/2009 | Martin et al. | |
| 2010/0185201 A1 | 7/2010 | Kim | |
| 2010/0234850 A1 | 9/2010 | Dees, Jr. et al. | |
| 2011/0029093 A1 | 2/2011 | Bojarski et al. | |
| 2011/0054483 A1 | 3/2011 | Howlett et al. | |
| 2011/0087332 A1 | 4/2011 | Bojarski et al. | |
| 2011/0152869 A1 | 6/2011 | Ek et al. | |
| 2011/0166661 A1 | 7/2011 | Boileau et al. | |
| 2011/0238071 A1 | 9/2011 | Fernandez-Scoma | |
| 2012/0053588 A1 | 3/2012 | Lozier et al. | |
| 2012/0150030 A1 | 6/2012 | Reach, Jr. et al. | |
| 2012/0209394 A1 | 8/2012 | Bojarski et al. | |
| 2012/0271417 A1 | 10/2012 | Ek | |
| 2012/0316565 A1 | 12/2012 | Stark | |
| 2012/0330316 A1 | 12/2012 | Berelsman et al. | |
| 2012/0330317 A1* | 12/2012 | Berelsman .......... | A61F 2/30756 606/88 |
| 2013/0165939 A1 | 6/2013 | Ries et al. | |
| 2013/0172891 A1* | 7/2013 | Bake .................. | A61F 2/30756 606/80 |
| 2013/0173228 A1 | 7/2013 | Bake et al. | |
| 2013/0184820 A1 | 7/2013 | Schwartz et al. | |
| 2013/0185927 A1 | 7/2013 | Bake et al. | |
| 2013/0211410 A1 | 8/2013 | Landes et al. | |
| 2013/0211531 A1 | 8/2013 | Steines et al. | |
| 2014/0142643 A1 | 5/2014 | Bake et al. | |
| 2014/0208578 A1* | 7/2014 | Linderman .......... | A61F 2/30756 29/592 |
| 2014/0224070 A1 | 8/2014 | Bake et al. | |
| 2014/0243836 A1 | 8/2014 | Bake et al. | |
| 2014/0249781 A1 | 9/2014 | Bake et al. | |
| 2014/0277522 A1 | 9/2014 | Goldberg et al. | |
| 2015/0190151 A1 | 7/2015 | Budhabhatti et al. | |
| 2015/0230874 A1 | 8/2015 | Musuvathy et al. | |
| 2015/0320429 A1 | 11/2015 | Katrana et al. | |
| 2016/0089159 A1 | 3/2016 | Ardito et al. | |
| 2016/0100847 A1* | 4/2016 | Maxson ............. | A61B 17/1675 606/80 |
| 2016/0151076 A1 | 6/2016 | Bake et al. | |
| 2016/0199075 A1 | 7/2016 | Bake | |
| 2017/0100253 A1 | 4/2017 | Bake et al. | |
| 2017/0172744 A1 | 6/2017 | Bake et al. | |
| 2017/0172747 A1 | 6/2017 | Bake et al. | |

FOREIGN PATENT DOCUMENTS

| | | |
|---|---|---|
| EP | 1753365 B1 | 10/2007 |
| EP | 1864629 A2 | 12/2007 |
| EP | 2138110 A2 | 12/2009 |
| EP | 2389899 A1 | 11/2011 |
| EP | 2389905 A1 | 11/2011 |
| EP | 2389905 B1 | 5/2012 |
| EP | 2685905 A1 | 1/2014 |
| JP | H8-502681 A | 3/1996 |
| JP | H10504217 A | 4/1998 |
| JP | 2008-539814 A | 11/2008 |
| WO | WO-94/09730 A1 | 5/1994 |
| WO | WO-96/24302 A1 | 8/1996 |
| WO | WO-2006/091686 A2 | 8/2006 |
| WO | WO-2007/014164 A2 | 2/2007 |

(56) References Cited

FOREIGN PATENT DOCUMENTS

| WO | WO-2008/098061 A2 | 8/2008 |
|----|-------------------|--------|
| WO | WO-2008/101090 A2 | 8/2008 |
| WO | WO-2008/138137 A1 | 11/2008 |
| WO | WO-2009/108591 A1 | 9/2009 |
| WO | WO-2009/111626 A2 | 9/2009 |
| WO | WO-2010/099357 A1 | 9/2010 |
| WO | WO-2011/063257 A1 | 5/2011 |
| WO | WO-2012/129018 A1 | 9/2012 |
| WO | WO-2012/143531 A1 | 10/2012 |
| WO | WO-2013/030371 A9 | 3/2013 |

OTHER PUBLICATIONS

Office Action dated Jan. 25, 2018 issued in U.S. Appl. No. 15/324,351 with double-patenting rejections on p. 2-5.
Extended European Search Report dated Jun. 13, 2017 in European Patent Application No. 17155242.5.
Office Action dated May 13, 2015 issued in corresponding European patent application No. 12 755 990.4 (6 pages).
Notice of Rejection dated Feb. 19, 2018 issued in corresponding Japanese patent application No. 2017-500889 (2 pages) and its English-language translation thereof (3 pages).
Notification of Reasons for Refusal dated Sep. 20, 2018 issued in Japanese patent application No. 2017-500889 (2 pages) and its English-language translation thereof (3 pages).
Extended European Search Report dated Dec. 17, 2018 in European Patent Application No. 18189755.4.

\* cited by examiner

METHOD OF A RIG

CROSS-REFERENCE TO PRIOR APPLICATIONS

This application is a § 371 National Stage Application of PCT International Application No. PCT/EP2015/065780 filed Jul. 9, 2015, which claims priority to PCT/EP2014/064760 filed Jul. 9, 2014, each of which are herein incorporated by reference in their entirety.

TECHNICAL FIELD

Embodiments herein relates in general to the field of orthopedic surgery and to cartilage and/or bone resurfacing. Embodiments herein relates to a rig intended for guiding replacement of a part of a bone and/or cartilage portion and to a design method of such a rig. Further embodiments herein also relates to a design method of an implant, surgery kits, kits of tools and a method for replacing a portion of an articular surface of a joint.

BACKGROUND

In the surgical operation of implanting small implants it is critical that the implant is positioned in a precise manner. If the implant is offset from its intended position it may cause increased wear or load on the joint. For example, if the implant is tilted this may result in an edge that projects above the cartilage surface and causes wear on the opposing cartilage in the joint. Another example is when the implant is placed in a position with the surface of the implant projecting above the surface of the cartilage causing the joint to articulate in an uneven manner and increasing the load on an opposing point of the joint. For the patient, also small misplacements or deviations from an ideal position may result in pain, longer time for convalescence or even a surgical operation being done in vain and making it more difficult to repair the damage in the joint. A large burden is therefore placed on the surgeon not to misplace or misfit the implant. There is a need for a guide or rig which can guide the surgeon to place the implant in a precise manner and also which can guide the removal of damaged tissue. Further there is a need for a rig which is designed to fit various damages and still give reproducible and precise placement each time even if the placement of the damage varies.

PRIOR ART

Examples of prior art disclosing implants and tools for replacement of damaged cartilage are: EP 2 389 905 shows a design method for designing an implant and a tool kit.

WO208098061 and US20120271417 disclose an implant for replacing a portion of an articular surface, wherein the implant comprises a first, second and third segment, wherein the first and the second segment partially overlap and the third and the second segment partially overlap. The implant is inserted by a guide system wherein reaming of the articulate surface is guided by using a guide pin. A drill guide may be used to establish the axes of the guide pin with respect to the articular surface.

U.S. Pat. No. 8,062,302 discloses a guide comprising a block having a patient-specific surface and first and second drilling holes.

US20110152869 discloses a trochlea repair system having two working axes displaced from each other, wherein the two working axes are used to create two partially overlapping sockets. WO2010099357 discloses a system for repair of a defect in an articulate surface, comprising a guide block which may comprise an opening configured to allow the cutter to pass through the guide block.

Object of Embodiments Herein

The general object of embodiments herein is to solve the problem of providing a design method for a rig which enables precision in the insertion and positioning of an implant at an articular surface of a joint. The object of embodiments herein is also to provide a rig and an implant and a design method of an implant.

There is a need for a tool or rig that is designed to give precise guidance and support to the surgeon during the implant surgery of small implants. Further there is a need of a flexible design method for such a rig.

Embodiments herein further seek to solve the partial problems of:

Providing a method for cartilage replacement wherein an implant is firmly attached in the joint and is well integrated into the surface structure of the joint, in order to generate optimal repair of damaged tissue and cause minimum damage to the surrounding tissue.

Providing a design method for a rig to be used for positioning of an implant to be implanted in the joint, improving the positioning of the implant in order to generate optimal repair of damaged tissue and cause minimum damage to the surrounding tissue and aiding the surgeon in that positioning.

Providing an individual design of a rig.

By using the design method according to embodiments herein the surgeon can get a precise way to place an implant in the joint using the design method of the rig and using the rig according to embodiments herein, The system according to embodiments herein wherein rig channel shapes may be built individually depending on cartilage damage and location of damage in the joint and by selecting from different sizes of circular shapes 303 or substantially circular shapes, partly overlapping each other in combinations which may be individually selected for one patient, allows the surgeon to choose an implant which fits the size and shape of the bone and/or cartilage damage or defect and gives the surgeon an easy to use design method and a tool set for making the excisions needed.

The design method according to embodiments herein allows for producing a rig and an implant which is easy to fit to an individual damage and an individual patient. The design build up in this method, comprising choosing size and at least two circular shapes and choosing thickness, surface shape, articular surface etc. for each implant, makes this solution unique and easy to individualize but still suitable for large scale industrial manufacturing. The circular shape build-up of the rig channels makes the rig also easy to use and gives an exact fit of each implant in every patient.

Advantages of Embodiments Herein

The area of the joint damage may not be easily covered by a single circular implant if the damaged area is elongate or is irregular or large in shape. Instead of using a number of separate implants or an implant requiring complicated bone removal techniques, using several different drills and tools, the design method of the surgical implant and the rig according to embodiments herein provides a solution which also utilizes a single rig anchored in place for the entire pre-drilling and drilling operation.

In one embodiment the same double-drill, the same pre drilling guide socket and the same depth adjustment socket is used for all drillings. This is made possible by a rig which permits shifting of the guide socket or adjustment socket from one side to the other side or the other sides of the hollow shell interior between drillings. In one embodiment a movable interior arcuate wall insert can also be inserted in each position to provide a complete circular cylinder for holding the pre-drilling guide socket for each drilling. The socket may also be adjustable. In another embodiment the movable insert is not arcuate but is a cylinder. In another embodiment no insert at all is used. Other similar embodiments are of course also possible.

According to one embodiment, this will create two identical peg holes and an exactly excavated cavity to fit an implant in the form of two intersecting circles of the same diameter. Merely removing the insert wall in the cylindrical interior then creates a shell, already securely rigged in location, for a rig for the oblong implant 1 with two pegs 23 and 23'. A handled gauge in the shape of the implant is inserted after drilling to check that the proper drilling depth has been reached. After all drillings have been made and depth checked, the drilling rig is removed.

SUMMARY

A design method for design of a rig and a tool module system comprising a rig are presented herein. The rig comprises a hollow tubular shell, and the interior of the shell defines at least first and second intersecting cylinders.

Embodiments of the design method comprises identifying a damage area, presenting a 3D view of the identified damage area and generating a 3D model of a virtual rig. The generating comprises virtually placing in 3D view a shape covering or partly covering damage area, and creating, based on the position of the virtually placed shape, a position of hollow tubular rig shell of the virtual rig. The method further comprises selecting the at least first and second intersecting cylinders of the virtual rig, based on the size and form of the virtually placed shape, and creating a positioning surface of the virtual rig which is a bone and/or cartilage-engaging end of the hollow tubular shell. The positioning surface is adapted to follow the surface surrounding the virtually placed shape when the virtual rig is placed in a virtual model of the joint. The method comprises producing a rig according to the virtually created rig.

In one embodiment the design method for a rig (600) for guiding surgery in a joint, wherein said rig (600) comprises a guide body in the form of a hollow tubular shell (510) configured to define at least first and second intersecting cylinders, the design method comprises;

identifying (101) a damage area (4) in said joint;
presenting a 3D view (9) of said identified damage area (4) in a virtual model of the joint;
generating a 3D model of a virtual rig, wherein the generating comprises virtually placing in said 3D view (9) a shape (303) at least partly covering said damage area (4) in said virtual model of the joint;
creating, based on the position of the virtually placed shape (303), a position of said hollow tubular shell (510) of the virtual rig;
selecting the at least first and second intersecting cylinders of the virtual rig, based on the size and form of the virtually placed shape (303);
creating a positioning surface (560) of the virtual rig as a bone and/or cartilage engaging end of said hollow tubular shell (510) and which positioning surface (560) is adapted to follow the surface of the joint surrounding the virtually placed shape when the virtual rig is placed in the virtual model of the joint;
producing a rig (600) according to the virtual rig.

In other embodiments herein, said hollow tubular shell of the guide body of the virtual rig is configured to define said at least first and second intersecting cylinders by a bore for each respective cylinder.

In other embodiments herein, said hollow tubular shell of the guide body of the virtual rig is configured to define said at least first and second intersecting cylinders by an insert guide having at least one bore for at least one of said cylinders.

In other embodiments herein, said hollow tubular shell of the guide body of the virtual rig and said insert are configured such that the insert is insertable in the hollow tubular shell in at least two different positions to define one of said at least two intersecting cylinders in each position.

In other embodiments herein, each of said first and second intersecting cylinders is provided with a circular cross-sectional profile.

In other embodiments herein, the circular cross-sectional profile of said first intersecting cylinder has a diameter being different from a diameter of the circular cross-sectional profile of said second intersecting cylinder.

In other embodiments herein, may the circular cross-sectional profile of the first intersecting cylinder have a diameter being equal to a diameter of the circular cross-sectional profile of the second intersecting cylinder.

In other embodiments herein, may the interior of the shell define first, second and third intersecting cylinders.

In other embodiments herein, may each of the first, second and third intersecting cylinders have a circular cross-sectional profile, and the diameter of each cylinder may be equal to one another.

In other embodiments herein, the design method may further comprise designing a movable insert comprising an arcuate wall which is adapted to be selectively insertable into the shell interior to complete the full circumference as desired.

In other embodiments herein, a movable insert may have a shape of a cylinder.

In other embodiments herein, said hollow tubular shell of the guide body of the virtual rig and an insert are configured such that the insert is insertable in the hollow tubular shell, and the interior cross-section of the shell and the exterior cross-section of the insert has at least one of:

a circular cross-section;
an elliptic cross-section;
a rectangular cross section;
a triangular cross-section;
and/or other symmetric, partially symmetric or non-symmetric cross-section.

In other embodiments herein, may the positioning surface of the rig be provided with multiple holes for pins for anchoring the rig securely in place on the surface to be repaired.

In other embodiments herein, the shape may comprise at least two circular shapes, and the method may further comprise placing at least two points each from where an axis will origin from. The points may be placed on the bone surface in the 3D view of the joint in or nearby the area of the bone and/or cartilage damage, or the points may be placed on a simulated bone surface which is a virtually created surface in or nearby the area of the bone and or cartilage damage. The method may further comprise selecting axe-distance and selecting diameter of the at least two circular shapes. The diameter of the circular shapes may be selected between 10-30 mm or for example 15-25 mm. The method may further comprise selecting coverage of the implant area over the cartilage and/or bone damage. The coverage may be between 50-100%. The method may further comprise selecting angles of the axes which originate from a point of the simulated bone surface. The axes may have an angle of 0-40 degrees in relation to a bone-axis which is normal in relation to a tangential plane of the simulated bone surface in that point.

In other embodiments herein, may each of the at least two circular shapes comprise an axis and wherein an overlap of the circular shapes depends on selection of diameter of the circular shapes in combination of selection of closeness of an axis of one circular shape in relation to another axis of another circular shape in combination with selection of desired coverage for the implant of the cartilage and/or bone damage.

In other embodiments herein, may each of the at least two circular shapes comprise an axis and an overlap of the circular shapes may depend on selection of diameter of between 1-3 cm of the circular shapes in combination with selection of an axe-distance of between 6 mm to 32 mm of one axis of one circular shape in relation to another axis of another circular shape in combination with selection of 50-100% of coverage for the implant body over the cartilage and/or bone damage.

In other embodiments herein, may identifying a cartilage and or bone area in a patient be performed by taking CT, CBCT, MRI images or the like of a joint of a patient and using these images to create a 3D view of the bone and or cartilage area and the bone and or cartilage damage using for example a software program useful for virtual 3D animation.

In other embodiments herein, may at least three circular shapes be placed partly overlapping, covering or partly covering the cartilage and or bone damage.

In other embodiments herein, the circular shapes may be in the size having a diameter of between 0.5-4 cm.

In other embodiments herein, may 2-5 circular shapes be placed partly overlapping, covering the bone and or cartilage damage.

In other embodiments herein, may virtually placing at least two circular shapes comprise virtually placing at least two points each from where an axis will origin from. The points may be placed on the bone surface of the joint in or nearby the area of the bone and or cartilage damage or the points may be placed on a simulated bone surface which is a virtually created surface in or nearby the area of the bone and or cartilage damage. The simulated bone surface may be a surface which preferably corresponds to a three dimensional, 3D, image of a bone surface in a healthy joint and wherein the points are in the center of the circular shapes. The circular shapes may partly overlap each other, and the axes may be placed so that the combined area spread of the circular shapes covers or partly covers the identified bone and or cartilage damage.

In other embodiments herein, may virtually placing at least two circular shapes be performed by placing the virtual circular shapes comprising axes in a predetermined angle in relation to each other.

In other embodiments herein, may each circular shape have an axis which is 90° in relation to the surface of the circular shape.

In other embodiments herein, may the area of the placed circular shapes include a surrounding area for letting an adjustment socket be inserted that will comprise the created hollow space in the rig.

In other embodiments herein, may at least three circular shapes be virtually placed in a row or other symmetry wherein at least one circular shape overlaps with at least two other circular shapes.

In other embodiments herein, may each circular shape have an axis at a point, and the axis may be 90° in relation to the normal of a tangent in a point on the virtual bone contact surface.

In other embodiments herein, may creating a virtual model of a rig further comprise creating a simulated bone surface in the 3D view, which mimics a non-damaged bone surface in a healthy patient and using the simulated bone surface as a base when creating the virtual model of the rig.

In other embodiments herein, a rig designed according to any the design method herein is provided.

In other embodiments herein, a method for placement of an implant in a bone and or cartilage area in a joint using the rig designed according to any of the methods herein is provided.

In other embodiments herein, a tool module system for replacing a portion of an articular surface of a joint is provided. The tool module system comprises a rig with at least a first and a second guide channel and an insert guide stop, wherein the insert guide stop is adapted to support instruments used in one of the guide channels of the guide tool and is configured to fit inside a part of the volume inside at least one of the guide channels.

Other embodiments herein is directed to a design method for design of an individually customized rig 600, the rig 600 having a hollow tubular shell 510 open at both ends, wherein the interior of the shell defines at least first and second intersecting circular cylinders and wherein the design method for the rig 600 comprises;

A first damage identification step 101 comprising identifying a bone and/or cartilage area 4 in a patient comprising a bone and/or cartilage damage 5 and presentation of a 3D view 9 of the identified area using a software program A second virtual model making step 14 comprising making a 3D model of a virtual rig comprising a step of virtually placing in the 3D view 9 at least two circular shapes 303, wherein each circular shape 303 partly overlaps at least one other circular shape 303', and wherein the combined area 20 of the circular shapes covers or partly covers the identified bone and/or cartilage damage 5 and wherein positioning data is used to create the position and interior of the hollow tubular rig shell 510 of the virtual rig which is open at both ends and wherein selection of at least first and second intersecting circular cylinder rig is based on the selected sizes of the circular shapes 303, or slightly larger, and wherein a positioning surface 560 of the virtual rig is created which is a bone and/or cartilage-engaging end of the hollow tubular shell 510 and wherein the positioning surface 560 is adapted to face and align to the surface structure surrounding the hollow circular shapes of the rig when the rig is placed in a virtual model of the joint.

A third production step 34 comprising producing a rig 600 according to the virtually created rig which is adapted to mimic the volume and shape according to the created virtual model of the rig.

Other embodiments herein comprises a design method for design of an individually customized rig 600 wherein the the interior of the shell defines first, second intersecting circular cylinders of equal diameter.

Other embodiments herein comprises a design method for design of an individually customized rig 600 wherein the interior of the shell defines first, second and third intersecting circular cylinders of equal diameter Other embodiments herein comprises a design method for designing an individually customized rig 600 to any of wherein a design step is added designing an arcuate wall which is adapted to be selectively insertable into the shell interior to complete the full circumference as desired.

Other embodiments herein comprises a design method, wherein the movable insert is not arcuate but is a cylinder.

Other embodiments herein comprises a design method for design of an individually customized rig 600, wherein the positioning surface 560 of the rig 600 is provided with multiple holes 61, 161 for pins anchoring the rig securely in place on the surface to be repaired.

Other embodiments herein comprises a design method for design of an individually customized rig 600 wherein a first selection step further comprises;

placing at least two points 19 each from where an axis 15 will origin from, the points 19 are placed on the bone surface 50 in the 3D view 9 of the joint in or nearby the area of the bone and/or cartilage damage 5 or the points 19 are placed on a simulated bone surface which is a virtually created surface in or nearby the area of the bone and/or cartilage damage 5 selecting axe-distance 53 selecting diameter of circular shapes, the diameter 302 of the circular shapes 303 are selected between 10-30 mm or for example 15-25 mm selecting coverage of the implant area 20 over the cartilage and/or bone damage 5, wherein the coverage may be between 50-100% and wherein a second selection step comprises;

Selection of the angles 25 of the axes 15 which originate from a point 19 of the simulated bone surface 51 and wherein the axes 15 and 15' have an angle 25 0-40 degrees in relation to a bone-axis 60 which is normal in relation to a tangential plane 28 of the simulated bone surface in that point 19, Other embodiments herein comprises a design method for design of an individually customized rig 600, wherein each circular shape 303 comprises an axis 15 and wherein the overlap 301 of the circular shapes 303 depends on selection of diameter 302 of the circular shapes 303 in combination of selection of closeness of an axis 15 of one circular shape 303 in relation to another axis 15' of another circular shape 303 in combination with selection of desired coverage for the implant of the cartilage and/or bone damage 5, Other embodiments herein comprises a design method for design of an individually customized rig 600, wherein each circular shape 303 comprises an axis 15 and wherein the overlap 301 of the circular shapes 303 depends on selection of diameter 302 of between 1-3 cm of the circular shapes 303 in combination of selection axe-distance 53 of between 6 mm to 32 mm of one axis 15 of one circular shape 303 in relation to another axis 15' of another circular shape 303' in combination with selection of 50-100% of coverage for the implant body over the cartilage and/or bone damage 5, Other embodiments herein comprises a design method for design of an individually customized rig 600, wherein identifying a cartilage and/or bone area 4 in a patient is performed by taking CT, CBCT, MRI images or the like of a joint of a patient and using these images to create a 3D view 9 of the bone and/or cartilage area 4 and the bone and/or cartilage damage 5 using for example a software program useful for virtual 3D animation.

Other embodiments herein comprises a design method for design of an individually customized rig 600, wherein at least three circular shapes 303 are placed partly overlapping, covering or partly covering the cartilage and/or bone damage 5, Other embodiments herein comprises a design method for design of an individually customized rig 600, wherein the circular shapes 303 are in the size having a diameter of between 0.5-4 cm.

Other embodiments herein comprises a design method for design of an individually customized rig 600, wherein 2-5 circular shapes 303 are placed partly overlapping, covering the bone and/or cartilage damage 5, Other embodiments herein comprises a design method for design of an individually customized rig 600, wherein creating a virtual model of a rig further comprises creating a simulated bone surface 53 in the 3D view 9, which mimics a non-damaged bone surface in a healthy patient and using the simulated bone surface 51 as a base when creating the virtual model of the rig.

Other embodiments herein comprises a design method for design of an individually customized rig 600, wherein virtually placing at least two circular shapes 303 in the second step 14 of the method according to embodiments herein comprises virtually placing at least two points 19 each from where an axis 15 will origin from, the points 19 are placed on the bone surface 50 of the joint in or nearby the area of the bone and/or cartilage damage 5 or the points 19 are placed on a simulated bone surface which is a virtually created surface in or nearby the area of the bone and/or cartilage damage 5, and wherein the simulated bone surface 51 is a surface which preferably corresponds to a three dimensional 3D image of a bone surface in a healthy joint and wherein the points 19 are in the center of the circular shapes 303, and wherein the circular shapes 303, partly overlapping each other, and wherein the axes 15 are placed so that the combined area spread 20 of the circular shapes 303 covers or partly covers the identified bone and/or cartilage damage 5, Other embodiments herein comprises a design method for design of an individually customized rig 600, wherein virtually placing at least two circular shapes 303 is performed by placing the virtual circular shapes 303 comprising axes 15 in a predetermined angle in relation to each other.

Other embodiments herein comprises a design method for design of an individually customized rig 600, wherein each circular shape has an axis which is 90° in relation to the surface 451 of the circular shape 303, Other embodiments herein comprises a design method for design of an individually customized rig 600, wherein the area of the placed circular shapes 303 including a surrounding area for letting an adjustment socket be inserted will comprise the created hollow space in the rig 600, Other embodiments herein comprises a design method for design of an individually customized rig 600, comprising virtually placing at least three circular shapes 303 in a row or other symmetry wherein at least one circular shape overlaps with at least two other circular shapes 303, Other embodiments herein comprises a design method for design of an individually customized rig 600, comprises virtually placing two circular shapes 303 wherein the two circular shapes overlap each other.

Other embodiments herein comprises a design method for design of an individually customized rig 600, wherein each circular shape 303 has an axis 15 at a point 19 and wherein the axis 15 is 90° in relation to the normal of a tangent in a point 19 on the virtual bone contact surface 51, Other embodiments herein comprises a rig 600 designed according to the design method mentioned above.

Other embodiments herein comprises a method for placement of an implant in a bone and/or cartilage area in a joint using the rig described in the specification.

Other embodiments herein comprises a tool module system for replacing a portion of an articular surface 6 of a joint wherein the tool module system comprises a rig 600 with at least a first and a second guide channel and an insert guide stop wherein the insert guide stop is adapted to support instruments used in one of the guide channels of the guide tool and configured to fit inside a part of the volume inside at least one of the guide channels.

A guide tool of the guide system according to embodiments herein comprising at least two guide holes or guide channels or openings to allow an in insert tool, for example a cutter or drill or rotary cutter, to pass through.

Other embodiments herein comprises a tool module system for guiding surgery in a joint, comprising:
- a rig (600) having a guide body in the form of a hollow tubular shell (510) configured to define at least first and second intersecting cylinders;
- a positioning surface (560) of the virtual rig being a bone and/or cartilage engaging end of said hollow tubular shell (510) and which positioning surface (560) is adapted to follow the surface of the joint surrounding an identified damage area in said joint.

Other embodiments herein comprises a tool module system, wherein said hollow tubular shell of the guide body of the rig is configured to define said at least first and second intersecting cylinders by a bore for each respective cylinder.

Other embodiments herein comprises a tool module system, wherein said hollow tubular shell of the guide body of the rig is configured to define said at least first and second intersecting cylinders by an insert guide having at least one bore for at least one of said cylinders.

Other embodiments herein comprises a tool module system, wherein said hollow tubular shell of the guide body of the rig and said insert are configured such that the insert is insertable in the hollow tubular shell in at least two different positions to define one of said at least two intersecting cylinders in each position.

Other embodiments herein comprises a tool module system, wherein each of said first and second intersecting cylinders is provided with a circular cross-sectional profile.

Other embodiments herein comprises a tool module system, wherein the circular cross-sectional profile of said first intersecting cylinder has a diameter being different from a diameter of the circular cross-sectional profile of said second intersecting cylinder.

Other embodiments herein comprises a tool module system, wherein the circular cross-sectional profile of said first intersecting cylinder have a diameter being equal to a diameter of the circular cross-sectional profile of said second intersecting cylinder.

Other embodiments herein comprises a tool module system, wherein said shell is configured to define a first, a second and a third intersecting cylinders.

Other embodiments herein comprises a tool module system, wherein each of said first, second and third intersecting cylinders have a circular cross-sectional profile, and wherein the diameter of each cylinder is equal.

Other embodiments herein comprises a tool module system, further comprising designing an insert guide adapted to be selectively insertable into the interior of said shell to configure the guide to define said intersecting cylinders.

Other embodiments herein comprises a tool module system, wherein said hollow tubular shell of the guide body of the virtual rig and an insert are configured such that the insert is insertable in the hollow tubular shell, and the interior cross-section of the shell and the exterior cross-section of the insert has at least one of:
- a circular cross-section;
- an elliptic cross-section;
- a rectangular cross section;
- a triangular cross-section;
and/or other symmetric, partially symmetric or non-symmetric cross-section.

Other embodiments herein comprises a tool module system, wherein the positioning surface (560) of said rig (600) is provided with a plurality of bores (61, 161) for pins for anchoring the rig securely in place on the surface to be repaired.

Other embodiments herein comprises a tool module system, wherein:
- the diameters (302) of the cylinders are selected between 10-30 mm or for example 15-25 mm; and/or
- a coverage, by the cross-section of said intersecting, cylinders of an implant area (20) over a cartilage and/or bone damage (5) is between 50-100%, and/or
- axes (15) and (15') of said cylinders have an angle (25) 0-40 degrees in relation to a bone-axis (60) which is normal in relation to a tangential plane (28) of the bone surface.

Other embodiments herein comprises a tool module system, wherein cross-sections of at least three circular shapes (303) are configured to partly overlap, covering or partly covering said cartilage and or bone damage (5).

Other embodiments herein comprises a tool module system, wherein the cross-sections of said cylinders have a diameter of between 0.5-4 cm.

Other embodiments herein comprises a tool module system, wherein cross-sections of 2-5 cylinders are placed partly overlapping, covering said bone and or cartilage damage (5).

Other embodiments herein comprises a tool module system, further being configured to define at least three cylinders in a row or other symmetry wherein the cross-section of at least one cylinder overlaps with the cross-section of at least two other cylinders.

BRIEF DESCRIPTION OF THE FIGURES

Embodiments of embodiments herein will now be described in more detail with reference to the appended drawings. Please note that the exemplified embodiments of embodiments herein disclosed in the figures is not to be interpreted limiting the scope of embodiments herein, FIG. 1, is an exemplified embodiment according to embodiments herein, not limiting of the scope of embodiments herein, disclosing a view of a 3D view of a patients' knee joint comprising a cartilage damage, the 3D view is created from MR data images or the like.

FIG. 8a is a view from one side and FIG. 8b is virtual implant from above.

DETAILED DESCRIPTION

Introduction

Figure 1:
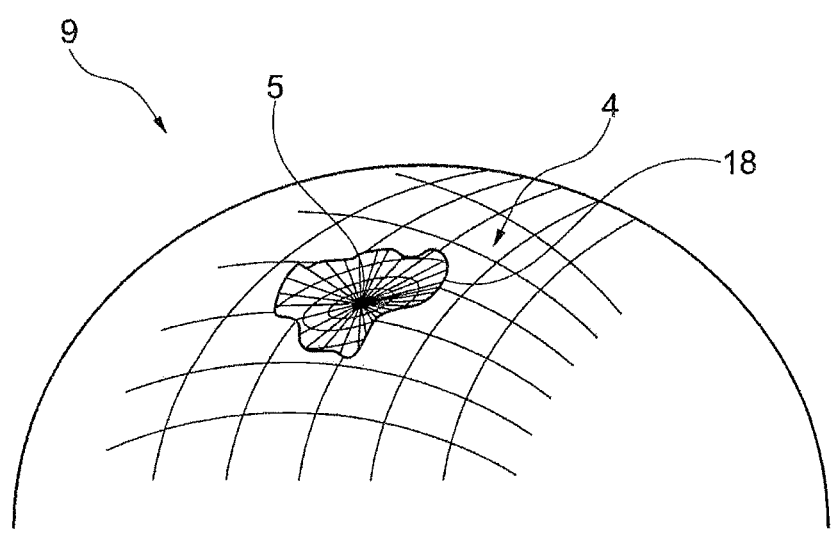

Embodiments herein relates to a design method for design of an individually customized rig 600 The rig 600 designed by the method according to embodiments herein is to be used for cartilage repair in a joint of a human or animal. The design method for design of an individually customized rig according to embodiments herein is described below.

The rig comprises a hollow tubular shell, and the interior of the shell defines at least first and second intersecting cylinders. The design method comprises identifying a damage area, presenting a 3D view of the identified damage area and generating a 3D model of a virtual rig. The generating comprises virtually placing in 3D view a shape covering or partly covering damage area, and creating, based on the position of the virtually placed shape, a position of hollow tubular rig shell of the virtual rig. The method further comprises selecting the at least first and second intersecting cylinders of the virtual rig, based on the size and form of the virtually placed shape, and creating a positioning surface of the virtual rig which is a bone and/or cartilage-engaging end of the hollow tubular shell. The positioning surface is adapted to follow the surface surrounding the virtually placed shape when the virtual rig is placed in a virtual model of the joint. The method comprises producing a rig according to the virtually created rig.

The design method for design of an individually customized rig 600, the rig 600 having a hollow tubular shell 510 open at both ends, characterized in that the interior of the shell defines at least first and second intersecting circular cylinders and wherein the design method for the rig 600 comprises the steps;

A first damage identification step 101 comprising identifying a bone and/or cartilage area 4 in a patient comprising a bone and/or cartilage damage 5 and presentation of a 3D view 9 of the identified area using a software program A second virtual model making step 14 comprising making a 3D model of a virtual rig comprising a step of virtually placing in the 3D view 9 at least two circular shapes 303, wherein each circular shape 303 partly overlapping at least one other circular shape 303', and wherein the combined area 20 of the circular shapes cover or partly cover the identified bone and/or cartilage damage 5 and wherein these positioning data is used to create the position and interior of the hollow tubular rig shell 510 of the virtual rig which is open at both ends and wherein selection of least first and second intersecting circular cylinders rig is based on the selected sizes of the circular shapes 303, or slightly larger, and wherein a positioning surface 560 of the virtual rig is created which is a bone and/or cartilage-engaging end of the hollow tubular shell 510 and wherein the positioning surface 560 is adapted to face and align to the surface structure surrounding the hollow circular shapes of the rig when the rig is placed in a virtual model of the joint.

A third production step 34 comprising producing a rig 600 according to the created virtually created rig which is adapted to mimic the volume and shape according to the created virtual model of the rig.

Figure shows the design method according to embodiments herein comprising three general steps; A first damage identification step 101, a second virtual model making step 14, a third production step 34, The design method according to embodiments herein allows for producing a rig which is easy to fit to repair an individual damage in a patient.

The design building up of this method comprising choosing size and at least two circular shapes and choosing overlap, thickness, articular surface etc for each rig makes this solution unique and easy to individualize, but still suitable for large scale industrial manufacturing.

The circular shape build-up of the implant makes the rig also easy to place by drilling and/or reaming giving an exact fit of each implant in every patient.

Damage Identification

A first damage identification step 101 comprises identifying a bone and/or cartilage area 4 in a joint of a patient comprising a bone and/or cartilage damage 5 and presentation of a 3D view 9 of the identified area using a software program. The first damage identification step 101 in the design method according to embodiments herein is to identify the bone and/or cartilage area 4 in a joint of a specific patient whom is in need of bone and/or cartilage repair. This is done from 2D images such as MR images. A 3D view 9 of a joint comprising a bone and/or cartilage area 4 and/or comprising the bone and/or cartilage damage 5 is created by taking 2D images of the joint and converting them into a 3D view 9, The bone and/or cartilage damage 5 can for example be identified in the 2D images which then are converted into a 3D view 9, Useful imaging techniques are for example Computed Tomography CT, Cone Beam Computed Tomography CBCT, Magnetic resonance imaging MM or other suitable techniques such as delayed Gadolinium-enhanced MRI of cartilage dGEMRIC techniques or the like, The taken 2D images of the joint are used to create a 3D model or view 9 of the patient's bone and/or cartilage and using for example a software program, for example a CAD animation program for example a radiography software program or the like is useful for 3D animation.

A joint representation-CAD animation model is created which is a 3D view 9 comprising the bone and/or cartilage area 4 based on images from the joint. This model is further comprising the bone and/or cartilage damage 5, A damage-representation CAD animation model which shows the bone and/or cartilage damage 5 may be created manually from 2D images by manually marking out damaged area pixels in each 2D image and from that create a 3D view 9 or the damage-representation CAD animation model may be a combination of the marked up 2D images.

In an automated process a computer program, for example a radiography software program, could be adapted to scan the images for predetermined characteristics of an area and/or spread, curvature and/or a location of bone and/or cartilage damage 2 in the image data and combine the automatically marked 2D images into a 3D view 9 also called the damage representation CAD animation model. The size of the area which is of interest to map or to create a 3D view 9 of is usually not depending of the size of the cartilage damage and the type of joint or bone part which is to be repaired, usually the surgeon does not know where in the joint the damage is located before taking images of the patients joint, therefore usually, images of the whole bone and/or cartilage area 4 of the joint are used to create a virtual 3D view 9, A virtual 3D view 9 is a joint representation CAD animation model which can be selected to show the bone and/or cartilage area 4, the bone and/or cartilage damage 5, placement of virtual rig or virtual implant etc.

In one embodiment according to embodiments herein a first damage identification step 101 of the design method according to embodiments herein comprises identifying a bone and/or cartilage area 4 in a patient by taking images of the injury or damage in the joint of a patient and then use these images of the individual patient's bone and/or cartilage area 4 to create a joint representation CAD animation model.

See for example FIG. 1, not limiting for the scope of embodiments herein, for one view of a 3D view 9 of a patient's knee joint and a cartilage and/or bone area 4 comprising a bone and/or cartilage damage 5 which is created from MR images or the like. FIG. 1 shows a 3D view 9 of a patient's knee joint comprising a bone and/or cartilage damage 5 wherein the borders around the bone and/or cartilage damage 18 are marked-up.

Joints in a human or animal which may be repaired by using the rig designed according to the design method according to embodiments herein can be selected from for example any of a knee, hip, shoulder, toe or finger joint.

Figure 9:
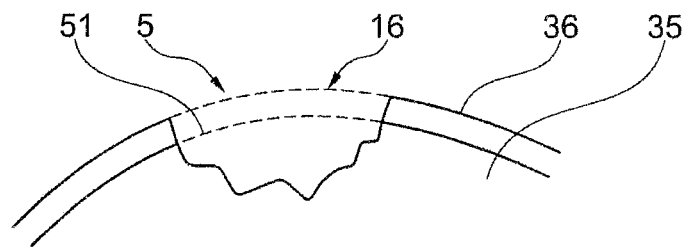
FIG. 9 is an exemplified embodiment according to embodiments herein, not limiting of the scope of embodiments herein and showing a bone and cartilage damage wherein a simulated repair surface 16 is created which is a surface which preferably corresponds to a three dimensional 3D image of a simulated healthy cartilage surface.
Figure 10:
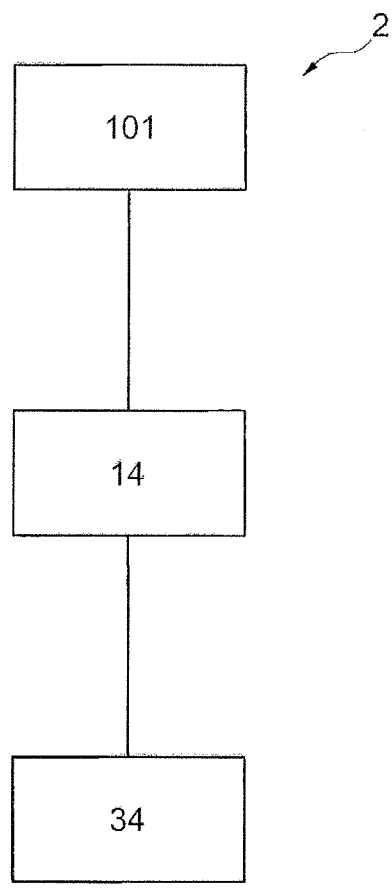
FIG. 10 is an exemplifying flow chart of a method according to embodiments herein.

FIG. 9 shows a 3D view 9 wherein a bone and/or cartilage damage is marked 5 and wherein a simulated cartilage repair surface 16 is marked out and wherein a simulated bone surface 51 is marked out and wherein the figure further comprises surrounding cartilage surface 36 and surrounding bone 35.

Virtual Model Making

The second step 14 in the method according to embodiments herein comprises a first step of selecting a surface comprising at least two circular shapes 301 which decides upon how much the combined area 20 of the circular shapes 301 cover or partly cover the identified bone and/or cartilage damage 5. This positioning data of the circular shapes 301 is used to create the position and interior of the hollow tubular rig shell 510 of the virtual rig which is open at both ends and wherein selection of at least first and second intersecting circular cylinders rig is based on the selected sizes of the circular shapes 303, or slightly larger, and wherein a positioning surface 560 of the virtual rig is created which is a bone and/or cartilage-engaging end of the hollow tubular shell 510 and wherein the positioning surface 560 is adapted to face and align to the surface structure surrounding the hollow circular shapes of the rig when the rig is placed in a virtual model of the joint.

In one embodiment, the second step 14 in the method according to embodiments herein comprises virtually placing at least two points 19 each from where an axis 15 will origin, the points 19 are placed on the bone surface 50 of the joint in or nearby the area of the bone and/or cartilage damage 5 or the points 19 are placed on a simulated bone surface 51 which is a virtually created surface and covering the area of the bone and/or cartilage damage 5, The simulated bone surface 51 is a surface which preferably corresponds to a three dimensional 3D image of a bone surface in a healthy joint. The points 19 are surrounded by selected circular shapes 303. The points 19 are centered in the circular shapes 301, the circular shapes 303, partly overlapping each other, and wherein the points 19 with the axes 15 are placed so that the combined area spread 20 of the circular shapes 303 covers or partly covers the identified bone and/or cartilage damage 5. The axes 15 are placed with a selected axe-distance 53 from each other. In one embodiment of embodiments herein the second step 14 in the method according to embodiments herein comprises a first selection of diameters 302 of the circular shapes 303, selection of how much the circular shapes 303 should cover of the bone and/or cartilage damage 5, selection of placement of axes 15 by selection of points 19 of intersection of the axes 15 on a simulated bone surface 51 or placement directly on a bone surface 50 in a 3D view of a joint. In another embodiment the diameter 302 of the circular shapes are selected simultaneously as the placement of the points 19 are made.

Different types of selections may be comprised in the second virtual model making step 14 and are in one embodiment according to the design method according to embodiments herein selected in the following order. In other embodiments the first, second and third selections can be made in any order or can be made simultaneously;

First Selections;

The first selections made in the second virtual model making step 14 according to embodiments herein can be made in any order or can be made simultaneously: and comprise placing at least two points 19 each from where an axis 15 will origin from, the points 19 are placed on the bone surface 50 of the joint in or nearby the area of the bone and/or cartilage damage 5 or the points 19 are placed on a simulated bone surface 51 which is a virtually created surface and covering the area of the bone and/or cartilage damage 5 selecting diameter of circular shapes, the diameter 302 of the circular shapes 303 are selected between 10-30 mm or for example 15-25 mm;

wherein the axe-distance 53 between the points 19 is for example between 6-32 mm or 7-20 mm or 7-12 mm;

selecting coverage of the implant area 7 over the cartilage and/or bone damage 5. The coverage is preferably 100% but may be between 50-100%.

Second Selections;

Selection of the angles 25 of the axes 15. Angles 25 in relation to simulated bone surface 51 or 50 and in relation to other axes.

Figure 11A:
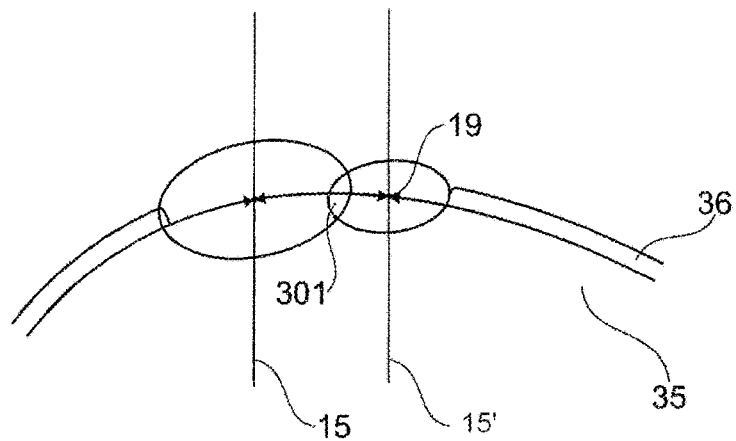
FIG. 11A is an exemplified embodiment according to embodiments herein, not limiting of the scope of embodiments herein and showing placement of axes of two circular shapes in a joint with a cartilage and bone damage.
Figure 11B:
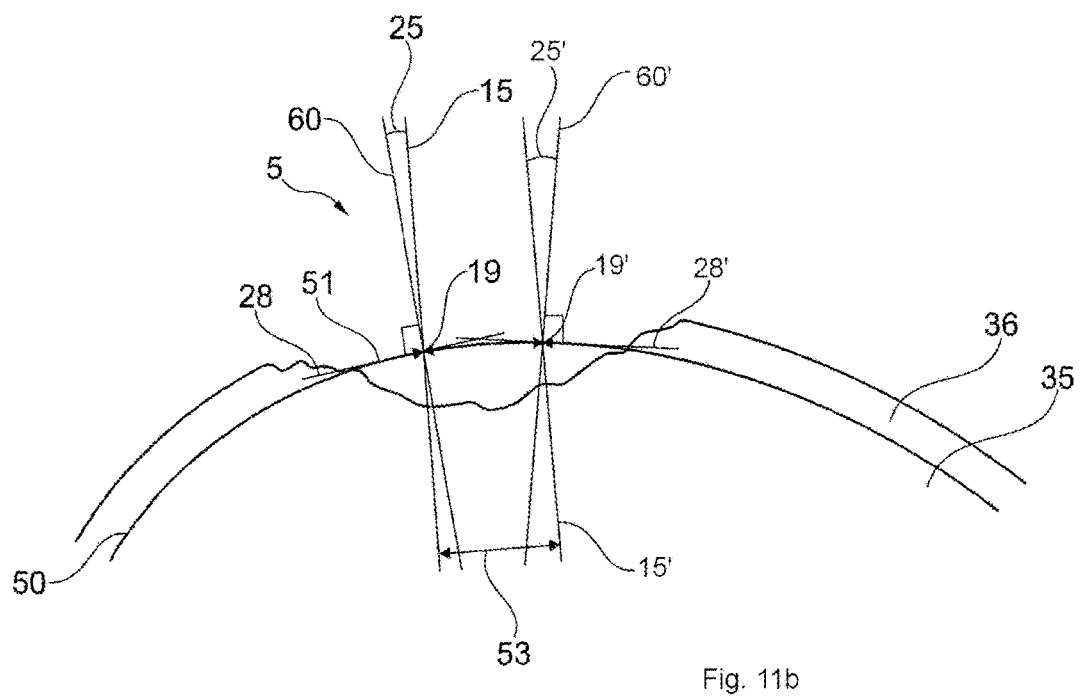
FIG. 11B is an exemplified embodiment according to embodiments herein, not limiting of the scope showing the placement of the axes in relation to each other with an axe-distance and in relation to a simulated bone surface wherein the axes originate from a point of the simulated bone surface. Alternatively, it is also possible to use a simulated cartilage surface for placement of the axes.

FIG. 11A shows an exemplified embodiment according to embodiments herein, not limiting for the scope of embodiments herein, showing placement of axes of two circular shapes in a joint with a cartilage and bone damage, the placement of the axes 15 and 15' is shown in relation to each other with an axe-distance 53 See FIG. 11B and in relation to a simulated bone surface 51 wherein the axes 15 and 15' originate from a point 19 of the simulated bone surface 51 and wherein the axes 15 and 15' have an angle 25, 25' in relation to an bone-axis 60 which is normal in relation to an tangential plane 28, 28' of the simulated bone surface in the point 19, FIGS. 11A and B further comprises cartilage 36, bone 35, bone surface 50, Third Selections;

In the third selection step of the second step 14 the height 710 of the hollow tubular rig shell 510 of the virtual rig is decided. The height of the hollow tubular shell 510 is selected depending on surrounding tissue and place of cartilage damage in order for ease of placement of the rig 600 during surgery and in order to have to make as little surgical intervention as possible. The height might be decided depending on where the implant is being placed. The height may vary depending on whether the implant is on for example the condylea or trochlea of a knee, being at least between 20-30 mm on the first and between at least 25-45 mm on the second. However a total variation of the height 710 between 10-90 mm is foreseen.

In the third selection step of the second step 14 the spread of an individually customized positioning surface 560 is also selected. The positioning surface 560 of the virtual rig is created which is a bone and/or cartilage-engaging end of the hollow tubular shell 510 and wherein the positioning surface 560 is adapted to face and align to the surface structure surrounding the hollow circular shapes of the rig when the rig is placed in a virtual model of the joint. The spread of the positioning surface 560 is selected depending on surrounding tissue and place of cartilage damage in order for ease of placement of the rig 600 during surgery and in order to have to make as little surgical intervention as possible. In one embodiment the spread is selected to cover an area in the joint with a curvature to guide the surgeon so that the rig 600 only can be placed in one way in the joint and thereby minimizing non-correct placement. The positioning surface 560 protrudes around the hollow tubular shell 510 so that the positioning surface gives the rig support during usage.

The hollow tubular rig shell 510 of the virtually created rig should preferably have a height 710 of in between 10-90 mm, especially 20-30 mm for condylea and 25-45 mm for trochlea of a knee.

In one embodiment the height of the hollow tubular rig shell 510 is decided upon by using the surfaces of the circular shapes 303 placed on a simulated bone surface 51 to create a cylindrical sphere presenting an elongation of a virtual view of the side wall of the circular shapes.

Different Types of First and/or Second and/or Third Selections in Second Virtual Model Making Step 14 which is Combinable According to the Methods In one embodiment according to embodiments herein the axe-distance 53 is between 6-32 or for example 7-20 or for example 7-12 mm.

In one embodiment according to embodiments herein the axe-distance 53 is larger than 8 mm. In one embodiment according to embodiments herein the axe-distance 53 is 8 mm. The placements of the points 19 and/or axes 15 and/or the selection of diameters 302 of the circular shapes 303 are done manually by an operator using a software program or automatically by a software program. In one embodiment at least two axes 15 are parallel in relation to each other. However even if the two axes are parallel the angle between the surface of the cartilage and the axes is in this embodiment not 90 grades because of the curvature of the cartilage. In other embodiments the axes 15 have different angles in relation to each other and also in relation to a simulated bone surface 51.

Figure 6:
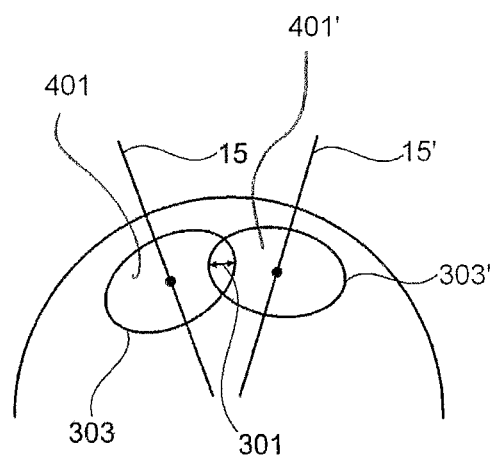
FIG. 6 is an exemplified embodiment according to embodiments herein, not limiting of the scope of embodiments herein and showing a view after placement of the circular shapes and design of circular shapes with non-parallel axes.

See for example FIG. 6 for an example according to embodiments herein wherein two circular shapes 303 are placed on a bone surface, with an overlap 301 and with non-parallel axes 15 and 15' and also showing the surface 301 of the circular shapes 303 and 303'.

In one embodiment the design method for design of an individually customized rig 600 according to any preceding claims, comprises virtually placing at least two circular shapes 303 is performed by placing two circular shapes 303 so that the diameter of the circular shapes 303 has a 20-90% or 40-70% overlap 301 in relation to the diameter of each circle.

The second virtual model making step 14 in the method according to one embodiment of embodiments herein comprises virtually placing at least two circular shapes 303, partly overlapping, covering or partly covering the identified bone and/or cartilage damage 5.

Figure 7:
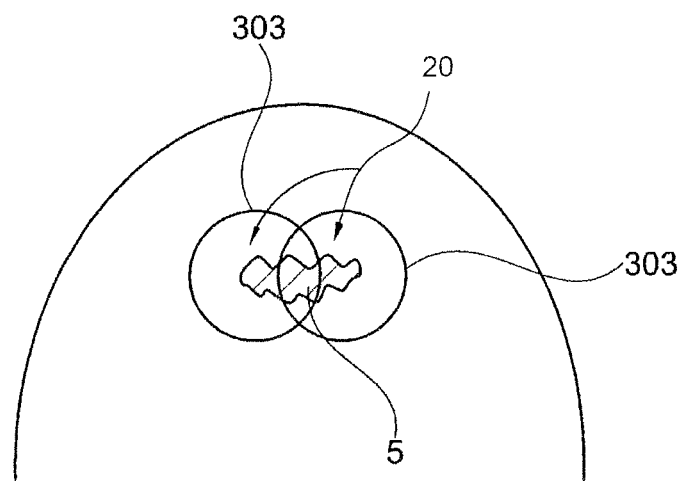
FIG. 7 is an exemplified embodiment according to embodiments herein, not limiting of the scope of embodiments herein and shows two circular shapes covering the bone and/or cartilage damage.

FIG. 7 illustrates an example according to embodiments herein of the second virtual model making step 14 and comprises two virtually placed circular shapes 303 spread out over an implant area 20 covering the identified cartilage and/or bone damage 5 in a 3D view 9.

In one embodiment the second virtual model making step 14 in the design method according to embodiments herein comprises;

virtually placing at least two circular shapes 303, partly overlapping, covering or partly covering the identified cartilage and/or bone damage 5 and virtually creating at least two directions of at least two circular shapes 303 in relation to the identified cartilage and/or bone area 4.

In one embodiment the different directions of the axes, for the angle of axis 15 and 15' is described. Axis 15 has an angle 25 of 0-40 degrees in relation to a bone axis 60 which is normal in relation to a tangential plane 28 of the simulated bone surface 51 or in relation to the bone surface 51 in the point 19, Axis 15' has an angle 25' of 0-40 degrees in relation to a bone-axis 60' which is normal in relation to a tangential plane 28 of the simulated bone surface 51 in the point 19' in a 3D view 9 of a virtually repaired articulate cartilage surface.

In one embodiment the different axes 15 and 15' of the circular shapes 303 have directions that are parallel to each other. In one embodiment the different axes 15 of the circular shapes 303 have different directions in relation to each other.

In one embodiment, the second step 14 in the method according to embodiments herein comprises of virtually placing at least two circular shapes 303, partly overlapping, covering the identified bone and/or cartilage damage 5, In one embodiment, the second step 14 in the method according to embodiments herein comprises of virtually placing at least two circular shapes 303, partly overlapping, covering the identified bone and/or cartilage damage 5 and wherein all the circular shapes 303 have identical or approximately the same diameter.

Figure 5:
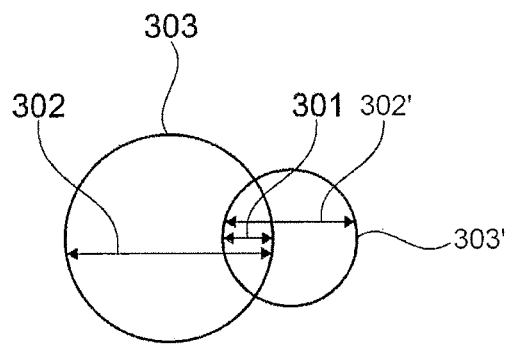
FIG. 5 is an exemplified embodiment according to embodiments herein, not limiting of the scope of embodiments herein and shows an example where the circular shapes have varying diameters.

In one embodiment, the second virtual model making step 14 in the method according to embodiments herein comprises of virtually placing at least two circular shapes 303, partly overlapping, covering the identified bone and/or cartilage damage 5 and wherein the different circular shapes 303 have diameters in varying sizes, for example one with smaller diameter than another. See for example FIG. 5 wherein one circular shape 303 has one diameter 302 and another circular shape 303' has a smaller diameter 302' and wherein the both circular shapes has an overlap 301.

In one embodiment the second virtual model making step 14 in the method according to embodiments herein comprises of virtually placing at least two circular shapes 303, partly overlapping, covering a part or covering the complete bone and/or cartilage damage 5 identified in images and presented in the 3D model of the bone and/or cartilage area 4 in the joint identified in the first step 101 of the design method according to embodiments herein.

The combined area 20 of the overlapping circular shapes 303 together with a surrounding area giving space to the drilling socket will together define the area 20 of the implant body 30 to be produced. In other words the area or cross section of the inside of the hollow tubular shell 510 means the sum of the spread of the shapes of the circular shapes 303.

Figure 2:
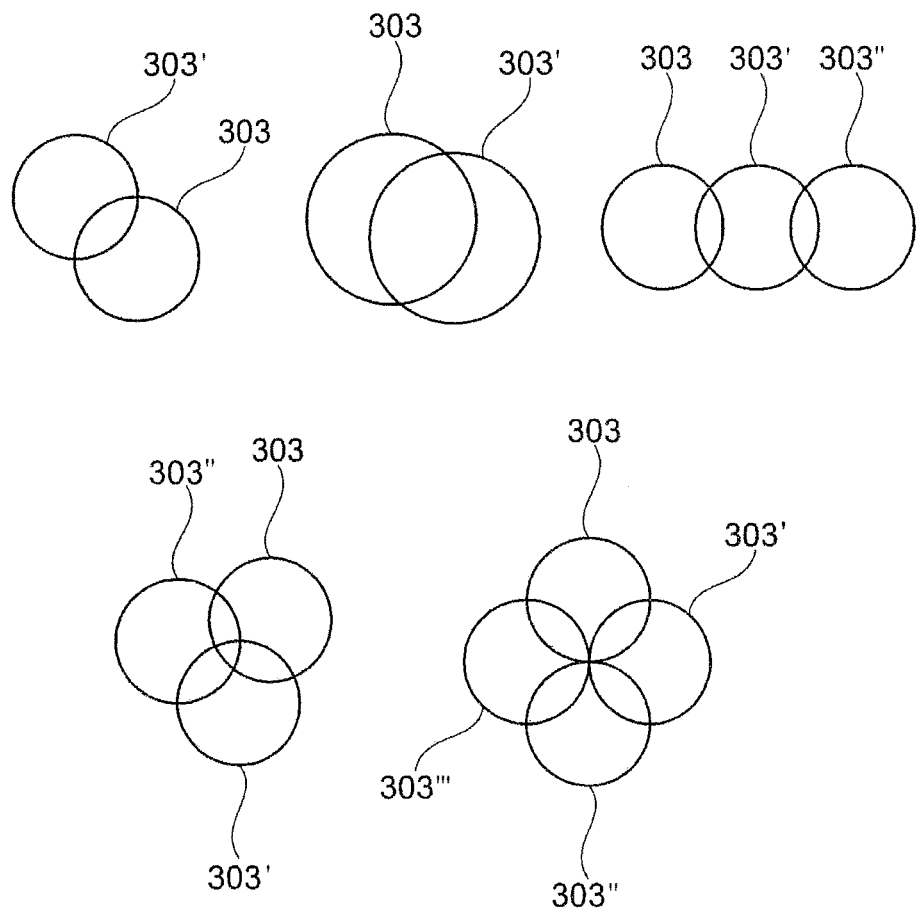
FIG. 2 is an exemplified embodiment according to embodiments herein, not limiting of the scope of embodiments herein and shows different examples of placement of the circular shapes in the first step of the design method in relation to each other.

The placement of the circular shapes 303 in relation to each other may be placement in a row or in symmetric groups or for example in an asymmetric order. For different examples of placement patterns of the circular shapes 303 see FIG. 2.

The placement pattern is selected depending on for example the placement of the bone and/or cartilage damage 5, and/or the size of the bone and/or cartilage damage 5 and/or the spread of the bone and/or cartilage damage 5 and/or the depth of the bone and/or cartilage damage 5. The overlap 301 of the circular shapes 303 is in one embodiment of embodiments herein performed so that the diameter of the circular shapes 303 has a 20-90% overlap 301 or for example 30-80% or for example 40-70% in relation to the diameter 302 of each overlapping circle.

The overlap 301 of the circular shapes 303 is in one embodiment of embodiments herein performed so that the diameter of the circular shapes 303 has at least 40% overlap 301 in relation to the diameter of each overlapping circle.

The diameters of the circular shapes 303 303 according to embodiments herein are between 5-30 mm or between 10-25 mm or for example between 15-25 mm.

Figure 3:
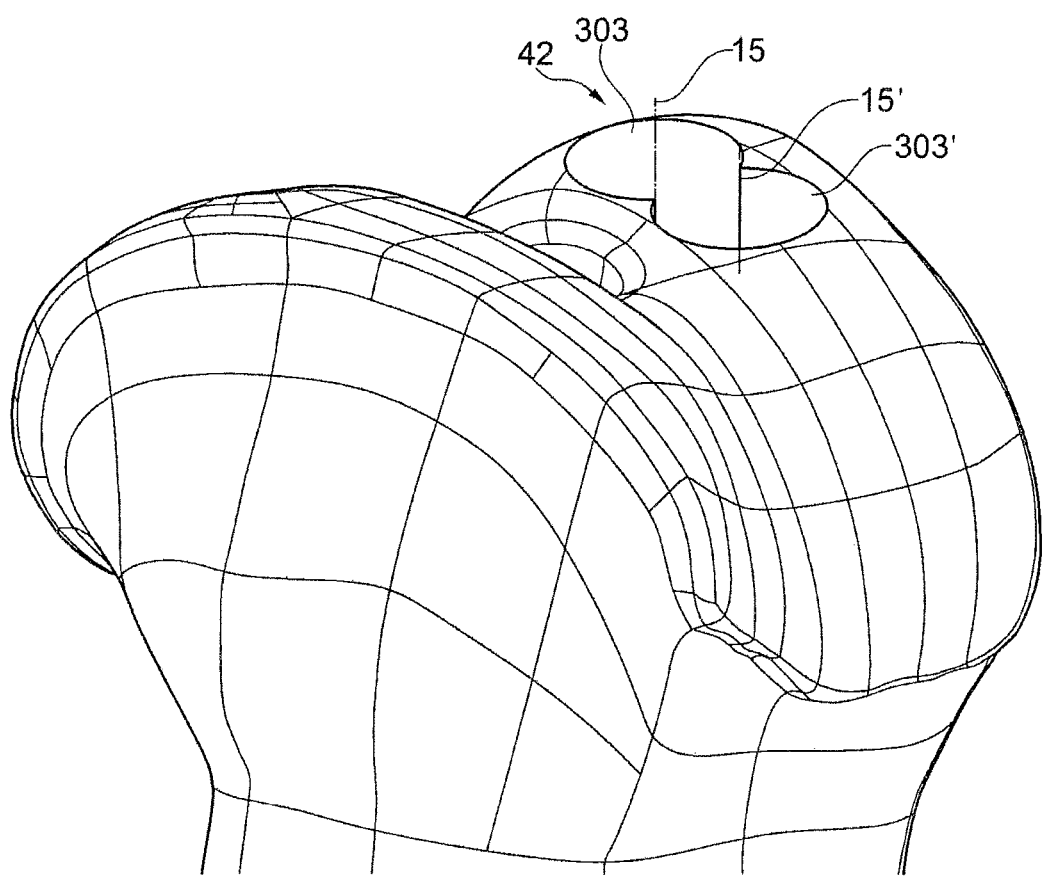
FIG. 3 is an exemplified embodiment according to embodiments herein, not limiting of the scope of embodiments herein and shows an virtual implant placed in a knee.
Figure 8A:
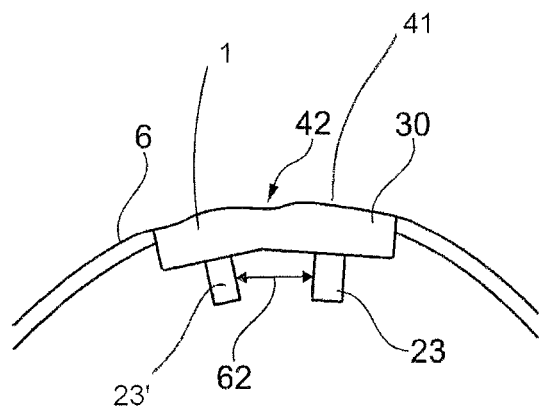
FIGS. 8a and 8b is an exemplified embodiment according to embodiments herein, not limiting of the scope of embodiments herein and showing the virtual model of the implant placed at the implantation site and comprising a simulated cartilage surface 6 of the implant 1 which simulates the cartilage surface before the cartilage damage.
Figure 8B:
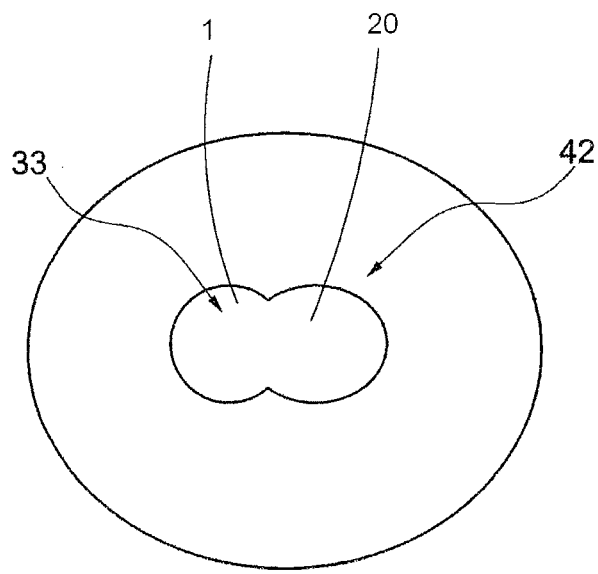

FIG. 3 shows one exemplified embodiment of embodiments herein, FIG. 3 shows a virtual implant 42 placed in a knee and wherein the virtual implant 42 comprises two circular shapes 303 placed so that they have an overlap and further the axes 15, 15' of the circular shapes 303, 303' of the implant is parallel in this example. This implant is placed with help of the rig designed by the design method according to embodiments herein, FIGS. 8a and 8b shown exemplified embodiment according to embodiments herein, not limiting for the scope of embodiments herein, showing the virtual model of the implant 42 placed at the implantation site and comprising a simulated cartilage surface 41 of the virtual model of the implant 42 which mimics the cartilage surface before a cartilage damage. Further the virtual implant model 42 in the example in FIG. 8a comprises a virtual implant body 30 and two extending post 23, see FIG. 8a.

FIG. 8a is a view from one side and FIG. 8b is a view of a virtual model of the implant 42 from above and wherein the area 20 of the implant to be produced is shown.

The rig according to embodiments herein may further comprise a wall insert 610, The guide tool of the guide system according to embodiments herein comprises at least two guide holes or guide channels or openings to allow a in insert tool, for example a cutter or drill or rotary cutter, to pass through. The design of the wall insert 610 is in one embodiment a part of the design method according to embodiments herein, The wall insert 610 is used in order to support the insert tools so that the channel inside the hollow tubular shell 510 of the rig 600 supports the insert tools during usage of the rig.

The insert tools are in one embodiment supported by parts of the walls of the guide channel inside the hollow tubular shell 510 in combination with a part of the sidewall of an wall insert 610, The wall insert 610 is a module which fits inside the guide channels by mimicking parts of the pattern of the guide channel inside area of the rig. The combination of parts of inside guide channel walls and part of sidewall of a wall insert 610 forms a round or cylindrical shaped guide hole, hereby called the active guide hole or guide channel. The active guide channel is a guide channel that may be used for insertion of insert tools at that time.

The active guide channel is changed by moving around the wall insert 610 in the inside area of the guide channels. By moving around the wall insert 610 to guide or support another guide channel in the guide tool, new active guide channels are formed. It is also possible to use several inserts of different sizes in parallel instead of adjusting the insert during the work.

In another embodiment the movable insert is not arcuate but is a cylinder.

In another further embodiment no insert at all is used. Other similar embodiments are of course also possible.

The wall insert 610 when placed in the rig channel, efficiently blocks guide channels not in use and the wall insert 610 forms, together with the inside walls of the active guide channel, a cylinder shaped wall around an active guide channel of the rig 600, Embodiments herein may comprise a design method for a rig and a wall insert 610 which together make the surgeon drill or cutter used inside the guide forming excision sites which correspond to an implant structure. The guide channels in the guide are adapted so that the formed excision sites are partially overlapping each other. By using a guide tool according to embodiments herein the surgeon can get a precise way to make the excisions needed to place an implant in the joint. The system according to embodiments herein wherein implant shapes may be build selecting from different sizes of circular shapes 303 partly overlapping each other in combinations allows the surgeon to choose an implant which fits the size and shape of the cartilage damage or defect and gives the surgeon easy to use tool set for making the excisions needed.

Production Step

The design method according to embodiments herein involves a third production step 34 of producing a rig 600, The third production step 34 according to embodiments herein comprises producing a rig 600 having the shape and volume as the virtual rig planned and created in first damage identification step 101 and the second virtual model making step 14, Polyamide rigs produced with selective laser sintering SLS are especially useful. Other production techniques and other materials are also possible. Other similar polymers such as polypropylene, polyethylene, polystyrene, polymethylmetaacrylate PMMA, acrylonitrile butadiene styrene ABS and similar compounds can be used. The rig can also comprise any metal or metal alloy used for structural applications in the human or animal body, such as stainless steel, cobalt-based alloys, chrome-based alloys, titanium-based alloys, pure titanium, zirconium-based alloys, tantalum, niobium and precious metals and their alloys. If a ceramic is used, it can be a biocompatible ceramic such as aluminium oxide, silicon nitride or yttria-stabilized zirconia. The rig may contain parts that are made of other materials as well.

Use Method of the Rig 600 According to Embodiments Herein

Figure 13:
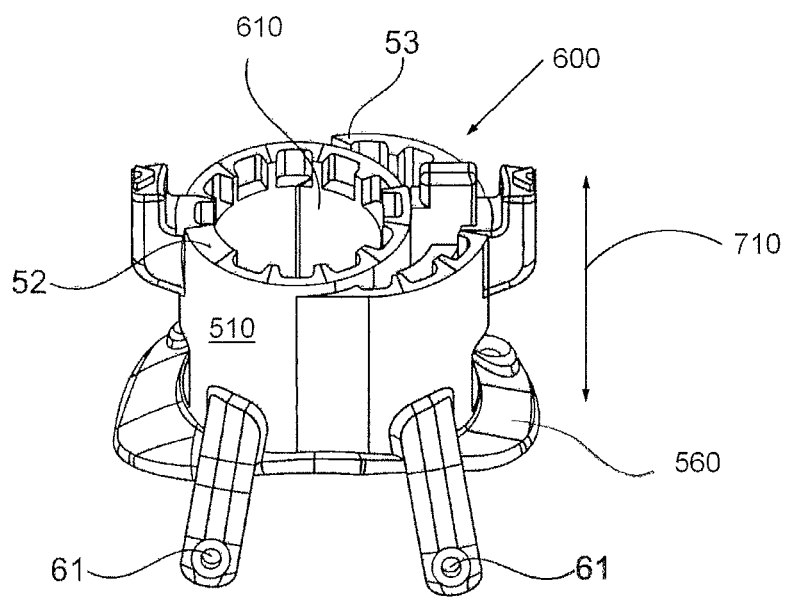
FIG. 13 shows a rig according to one embodiment of embodiments herein for a two peg-implant. The rig is mounted in place.

FIG. 13 shows an example of one embodiment of a rig according to embodiments herein which is used for all of the hole preparation. The rig comprises an elongated hollow shell 510 having the form of two intersecting overlapping circular cylinders 52, 53 of the same diameter and the hollow tubular rig shell 510 has a height 710 between 10-90 mm. The rig 600 can be formed to conform to the shape of the bone and cartilage area of the patient to be repaired or can be a standard rig. The rig is held securely in place on the condylar surface in this case by individually customized the positioning surface 560 and with pins not shown driven in through holes 61, to hold the rig securely in place throughout the entire drilling process.

Figure 4A:
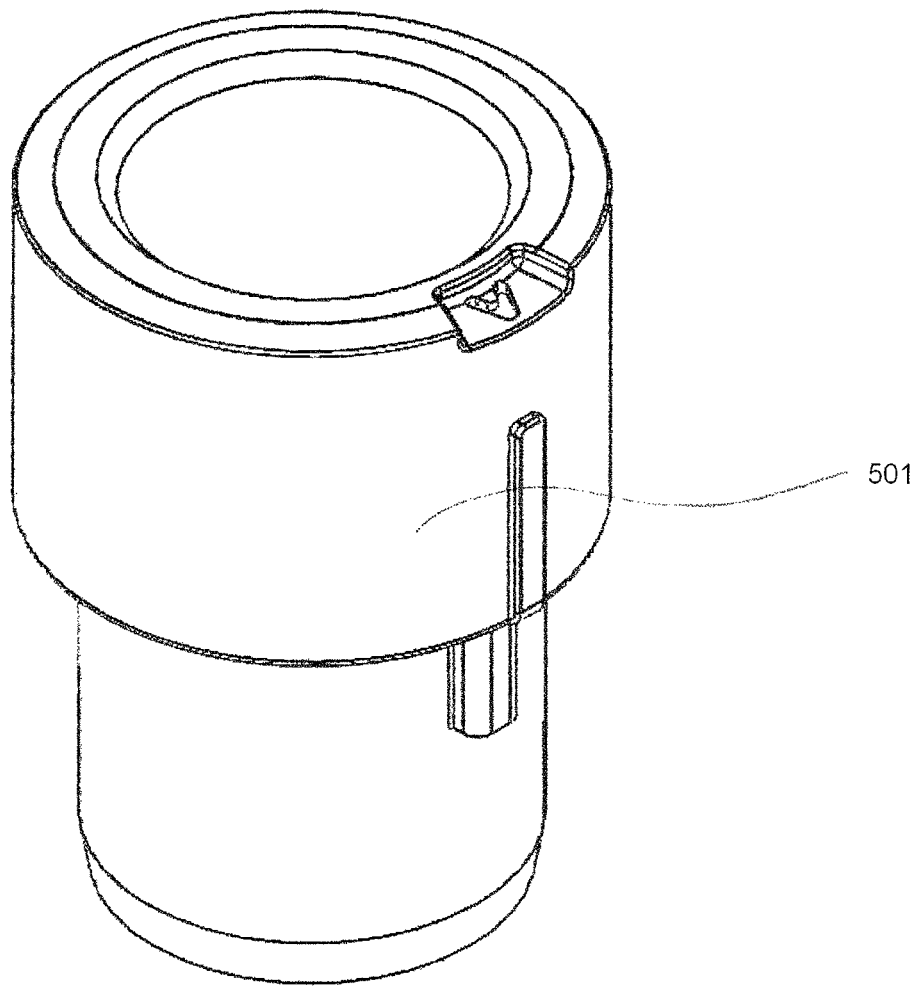
FIG. 4a shows a pre-drilling guide socket.
Figure 4B:
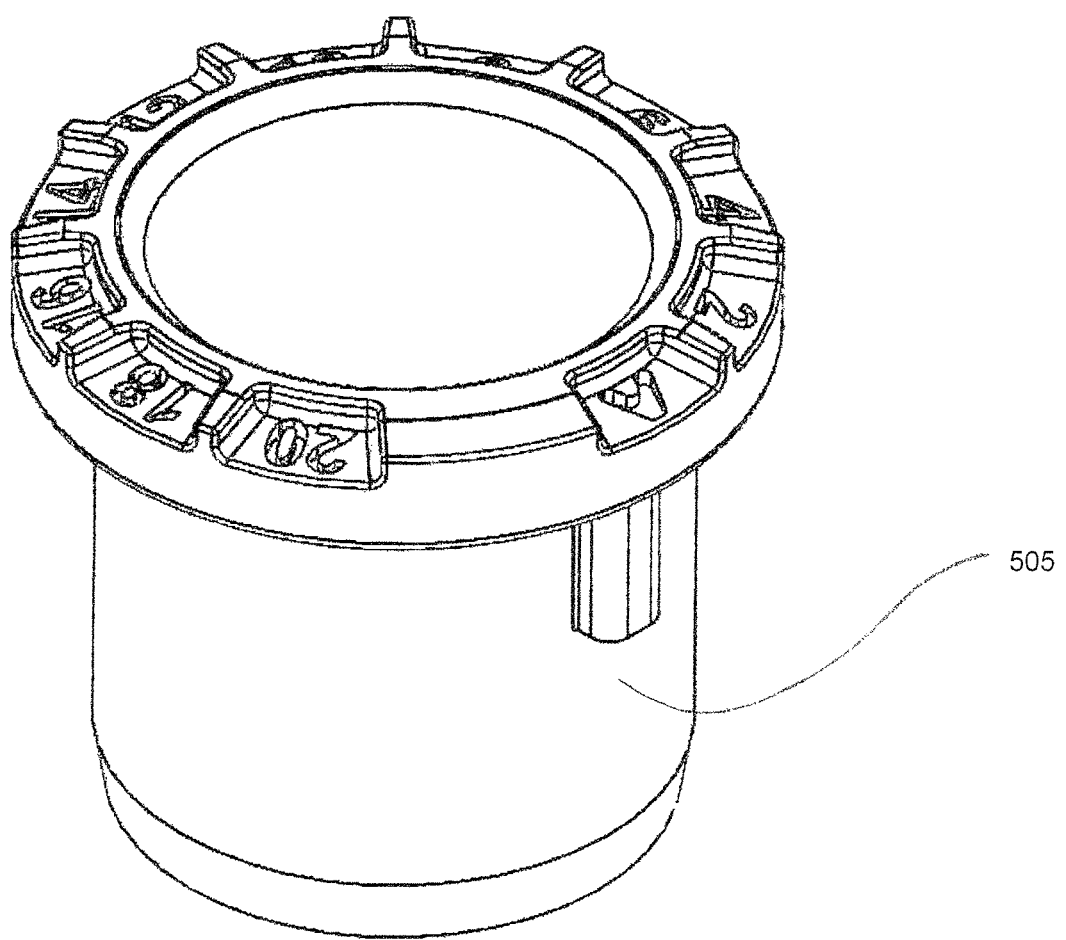
FIG. 4b shows a drilling depth adjustment socket.

After the pins have been driven in, the cutting and drilling process can begin, with a wall insert 610 inserted in one end of the hollow shell, leaving an entire first circular cylinder 52 at one end of the hollow tubular shell. At this time the surgeon may insert into the first circular cylinder a depth adjustment socket 505 FIG. 4b and then a sharp cylindrical hand knife, sized exactly to the interior of the adjustment socket 505, makes a preliminary circular sharp edged cut through the cartilage down to the bone. A circular bare bone area is left after this cartilage removal.

Figure 15:
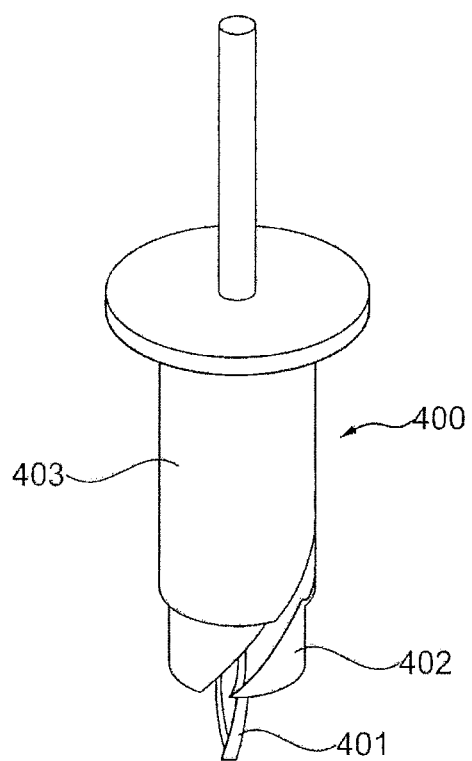
FIG. 15 shows an example of a double drill for use with the drilling rig according to embodiments herein.

In one embodiment, the surgeon uses a 17/4 mm double drill as shown schematically in FIG. 15. It has a central narrow 4 mm diameter bit 401, and a wider 17 mm diameter cutting bit 402, The outer lateral surface 403 of the double drill conforms to the circular cylinder, which securely holds the double drill to drill, in the same operation, a central 4 mm hole for the first peg 23 and a much shallower surrounding bore 17 mm in diameter in this example. A pre-drilling of the initial part of the peg hole in the bone can according to one embodiment be made using a guide socket 501 FIG. 4a, This improves the exact placement of the simultaneous drilling of the peg hole and the circular bare-bone area with the double drill FIG. 15, After removing the drill, and flushing out organic matter, the surgeon then slides the wall insert 610 out and inserts it in on the other side of the hollow shell, creating a complete circular cylindrical guide hole on the opposite side of the hollow shell.

The surgeon then inserts the adjustment socket and uses the same cylindrical knife in the newly created guide hole, to make a circular excision of the cartilage not a complete circle since the intersecting portion has already been removed in the previous step, The in this embodiment 17/4 mm double drill is then used again first with the guide socket 501 to pre-drill the peg hole and then with the adjustment socket 505 to double-drill the peg hole to its full depth and create the bare-bone circle, i.e. the 4 mm hole for the second peg and a second surrounding shallow bore which is of course also 17 mm in diameter.

These two drilling operations have created 4 mm peg holes and a space in the bone to exactly accommodate in this case a 17+17 implant of embodiments herein, The wall insert 610 is then completely removed. A handle-equipped gauge corresponding to the intersecting circular forms making up the implant, is used to make sure that the holes have been drilled to the proper depth in the bone. The rig is then removed and the implant pegs or extending posts 23 are inserted into their holes. For the cap of the implant to lodge exactly in the in this case 17+17 shallow cavity removed from the surface of the bone it is usually necessary to carefully tap the cap, preferably on top of the first peg, with interference fit, with a hammer via a special mandrel. The first, slightly thicker peg, is tapped down into its hole while the second peg, slightly narrower, slides easily into its hole. The larger diameter part of the 17/4 mm drill in this example has a rim to excavate a peripheral slot slightly deeper than the 17 mm shallow cavity, to accommodate the peripheral ridge 47 of the implant, helping to hold the implant securely in place during healing and subsequent loading during use.

Thus the rig, which can be form-fitted to the shape of the individual patient's cartilage surface in this example, is placed over the damaged area of the condyle and is anchored securely in place, in this particular non-limiting example, by driving in four pins not shown into holes 61 in the condyle shaped lower end of the rig 600, It is now securely in place for the entire drilling operation, which be simplified greatly and made much more exact and less dependent on the artistry of the surgeon, which may vary from day to day.

After drilling of the holes, the pins are pulled out and the rig is removed from the site, for implantation of the implant and reconstitution of the joint with the new implant.

It will be understood by the person skilled in the art that the rig as claimed can be supplemented with an insert sleeve to make one of the circular cylinders of a small diameter, e.g. from 17 to mm in diameter, to accommodate an implant having the form of two intersecting circles of slightly different diameters, for example +17 millimeters. Of course also rigs with a specific predecided fixed diameter may be prepared.

Figure 14A:
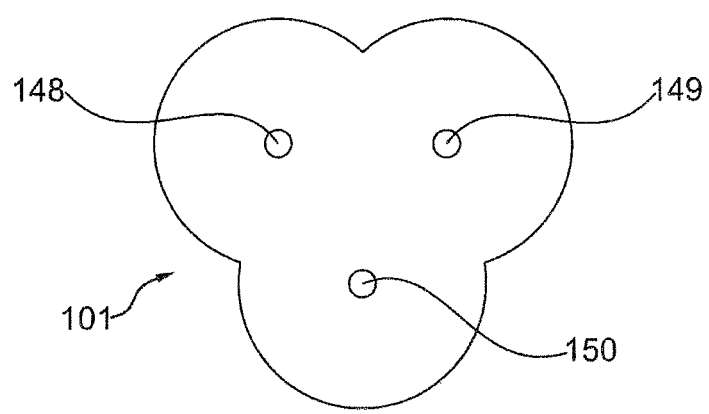
FIG. 14a shows one embodiment of a three-pegged implant having the form of three identical intersecting circles.

It will of course also be possible, within the scope of embodiments herein to create an implant in the form of three, or more, intersecting circles, to cover bone damage of more irregular shape. One such three-circle implant 101 is shown from below in FIG. 14a showing three pegs 148, 149 and 150, In this example peg 148 has an interference fit diameter in relation to the common nominal diameter of all three pegs and the other two pegs 149 and 150 have clearance fit diameters in relation to the common nominal diameter.

Figure 14B:
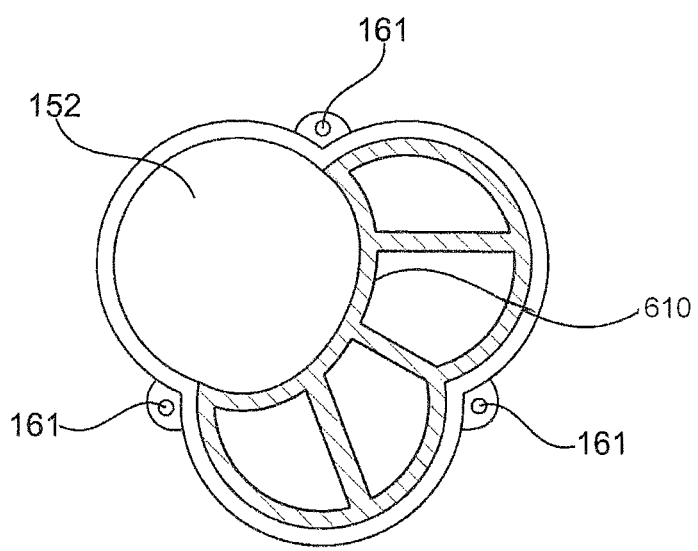
FIG. 14b shows one embodiment of a rig with wall insert for a three-peg implant, seen from above.

The rig for this three-circle implant is shown from above in FIG. 14b. The rig is held in place on the bone by pins not shown inserted through holes 161, The wall insert 610, completes the first circular cylinder 152 covering the remaining portions of the other two circular cylinders. When the first circular drilling has been made the wall insert 610 is pulled out, rotated 120 degrees and is inserted again to provide a drill guide for the next circle drilling with the same double drill, which in one embodiment can be the same 17/4 drill used together with the two-circle rig. After rotation 120 degrees again and drilling, a three pegged implant is inserted. As stated above, this insert has one peg which is of interference fit dimension in relation to its nominal diameter in this case 4 mm and the other two pegs are of clearance fit.

FIG. 15 shows an exemplary 4/17 double drill for use with the multiple circle rigs described above or with a previously known single circle rig, The double drill has a 4 mm central bit 401 for creating the hole for the peg and a wider cutting surface 402 for creating the 17 mm shallow hole. One of the advantages of embodiments herein is that the same double drill can be used for single, double or triple or more intersecting circle shaped implants, used twice or three times as the case may be for the two embodiments shown here. According to the example in FIG. 17 the hole is more shallow then the peg. According to other examples it could also be deeper than the peg.

Figure 16A:
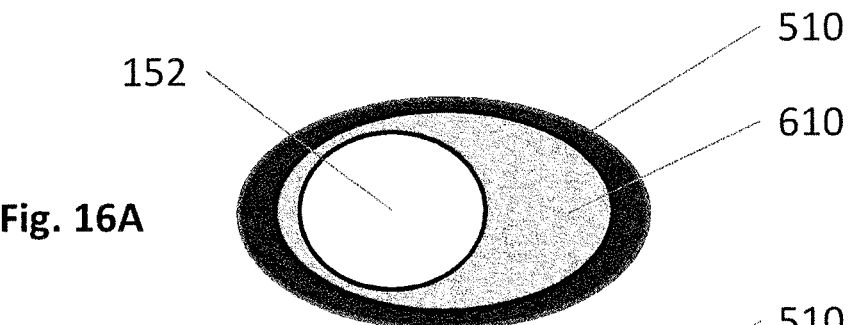
FIGS. 16A-16C show examples of cross-sections of a rig with inserts in accordance with embodiments herein.
Figure 16B:
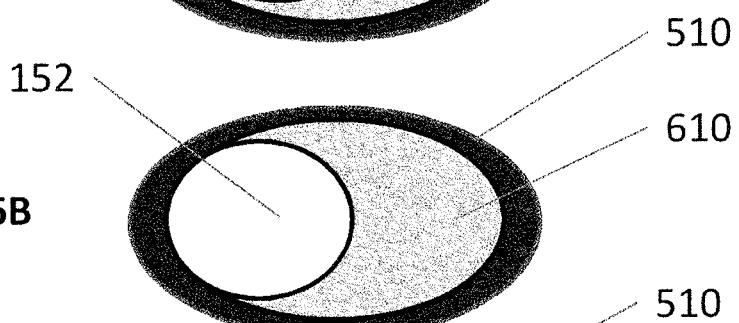
Figure 16C:
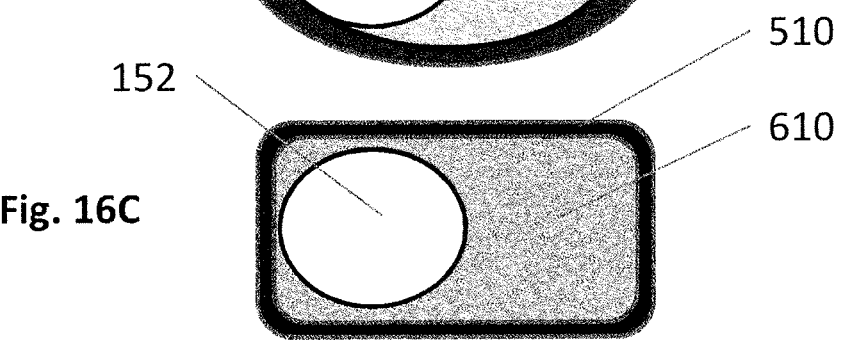

FIGS. 16A-16C show examples of cross-sections of a rig with inserts in accordance with embodiments described herein. FIG. 16A-16C show examples of a cross-section of an embodiment of the hollow tubular shell 510 of a rig with an insert 610 configured to define a cylinder having a cross-section 152. In a first position as shown in the figure the insert 610 defines the first cylinder. When the insert 610 is taken out, turned 180 degrees and inserted again in the shell 510 it defines the second cylinder. In embodiments illustrated by FIGS. 16A and 16B, the interior cross-section of the shell and the cross-section of the insert are elliptic. In FIG. 16A, the cross-section of the cylinders is defined by a bore in the insert 610. In FIG. 16B, a segment of the cross-section of the cylinder defining bore is part of the shell 510 and the other segment is part of the insert 610. In FIG. 16C, the interior cross-section of the shell 510 and the cross-section of the insert are rectangular. In other embodiment, other cross-sections preferably are provided or conceivable, e.g. symmetrical, partly symmetrical or non-symmetrical cross-sections.

Figure 16D:
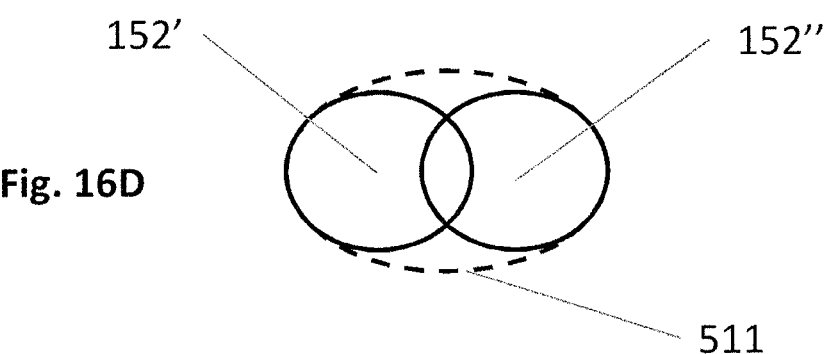
FIG. 16D shows an example of contours of cross-sections as defined by the rig and insert of FIG. 16B.

FIG. 16D shows an example of contours of cross-sections as defined by the rig and insert of FIG. 16B.

Figure 12:
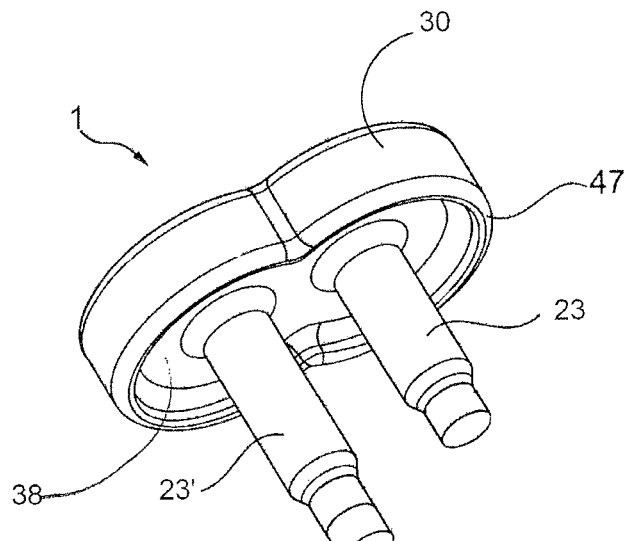
FIG. 12 shows a two-pegged implant.

FIG. 12 shows an exemplified embodiment of an implant 1 according to embodiments herein, having two circular shapes, having two extending posts 23, 23' or pegs and a protruding edge 47 surrounding the implant body 30, This example is directed to an example wherein the two circular shapes have the same diameters.

The foregoing disclosure is not intended to limit the present invention to the precise forms or particular fields of use disclosed. It is contemplated that various alternate embodiments and/or modifications to embodiments herein, whether explicitly described or implied herein, are possible in light of the disclosure. Accordingly, the scope of protection is defined only by the claims.

The invention claimed is:

1. A method for designing and making a rig for guiding surgery in a joint,
   wherein said rig comprises a guide body in the form of a hollow tubular shell configured to define at least first and second intersecting cylinders,
   the method comprising:
   identifying a damage area in said joint;
   presenting a 3D view of said identified damage area in a virtual model of the joint;
   generating a 3D model of a virtual rig, wherein the generating comprises virtually placing in said 3D view a shape at least partly covering said damage area in said virtual model of the joint;
   creating, based on the position of the virtually placed shape, a position of said hollow tubular shell of the virtual rig;
   selecting the at least first and second intersecting cylinders of the virtual rig, based on the size and form of the virtually placed shape;
   creating a positioning surface of the virtual rig as a bone and/or cartilage engaging end of said hollow tubular shell and which positioning surface is adapted to follow the surface of the joint surrounding the virtually placed shape when the virtual rig is placed in the virtual model of the joint; and
   making a rig according to the virtual rig,
   wherein said hollow tubular shell of the guide body of the virtual rig is configured to define said at least first and second intersecting cylinders by a bore for each respective cylinder; or
   wherein said hollow tubular shell of the guide body of the virtual rig is configured to define said at least first and second intersecting cylinders by an insert guide having at least one bore for at least one of said cylinders, and wherein said hollow tubular shell of the guide body of the virtual rig and said insert are configured such that the insert is insertable in the hollow tubular shell in at least two different positions to define one of said at least two intersecting cylinders in each position; or
   wherein each of said first and second intersecting cylinders is provided with a circular cross-sectional profile, and:
      wherein said circular cross-sectional profile of said first intersecting cylinder has a diameter being different from a diameter of the circular cross-sectional profile of said second intersecting cylinder, or
      wherein the circular cross-sectional profile of said first intersecting cylinder has a diameter being equal to a diameter of the circular cross-sectional profile of said second intersecting cylinder.

2. The method according to claim 1, wherein said shell is configured to define a first, a second and a third intersecting cylinders,
   wherein each of said first, second and third intersecting cylinders have a circular cross-sectional profile, and
   wherein the diameter of each cylinder is equal.

3. The method according to claim 1, further comprising designing an insert guide adapted to be selectively insertable into the interior of said shell to configure the guide to define said intersecting cylinders.

4. The method according to claim 1, wherein said hollow tubular shell of the guide body of the virtual rig and an insert are configured such that the insert is insertable in the hollow tubular shell, and the interior cross-section of the shell and the exterior cross-section of the insert has at least one of:
   a circular cross-section;
   an elliptic cross-section;
   a rectangular cross section;
   a triangular cross-section; or
   other symmetric, partially symmetric or non-symmetric cross-section.

5. The method according to claim 1, wherein the positioning surface of said rig is provided with a plurality of bores for pins for anchoring the rig securely in place on the surface to be repaired.

6. The method according to claim 1, wherein said shape comprises at least two circular shapes, the method further comprising:
  placing at least two points each from where an axis will origin from, the points are placed on the bone surface in the 3D view of the joint in or nearby the area of the bone and or cartilage damage or the points are placed on a simulated bone surface which is a virtually created surface in or nearby the area of the bone and or cartilage damage;
  selecting axes-distance;
  selecting the diameters of said at least two circular shapes, wherein the diameters of the circular shapes are selected between 10-30 mm or for example 15-25 mm;
  selecting coverage of implant area over the cartilage and/or bone damage, wherein the coverage is between 50-100%; and
  selecting angles of the axes which originate from a point of said simulated bone surface and wherein the axes and have an angle 0-40 degrees in relation to a bone-axis which is normal in relation to a tangential plane of the simulated bone surface in that point.

7. The method according to claim 6, wherein each of said at least two circular shapes comprises an axis and wherein an overlap of the circular shapes depends on selection of diameter of the circular shapes in combination of selection of closeness of an axis of one circular shape in relation to another axis of another circular shape in combination with selection of desired coverage for the implant of the cartilage and/or bone damage; or
  wherein each of said at least two circular shapes comprises an axis and wherein an overlap of the circular shapes depends on selection of diameter of between 1-3 cm of the circular shapes in combination of selection of an axes-distance of between 6 mm to 32 mm of one axis of one circular shape in relation to another axis of another circular shape in combination with selection of 50-100% of coverage for the implant body over the cartilage and/or bone damage.

8. The method according to claim 6, wherein virtually placing at least two circular shapes comprises virtually placing at least two points each from where an axis will origin from, the points are placed on the bone surface of the joint in or nearby the area of the bone and or cartilage damage or the points are placed on a simulated bone surface which is a virtually created surface in or nearby the area of the bone and or cartilage damage, and wherein the simulated bone surface is a surface which preferably corresponds to a three dimensional (3D) image of a bone surface in a healthy joint and wherein the points are in the center of the circular shapes, and wherein the circular shapes, partly overlapping each other, and wherein the axes are placed so that the combined area spread of the circular shapes covers or partly covers said identified bone and or cartilage damage.

9. The method according to claim 1, wherein at least three circular shapes are placed partly overlapping, covering or partly covering said cartilage and or bone damage; or
  wherein said shapes are circular having a diameter of between 0.5-4 cm; or
  wherein 2-5 circular shapes are placed partly overlapping, covering said bone and or cartilage damage; or
  combinations thereof.

10. The method according to claim 1, wherein virtually placing at least two circular shapes is performed by placing the virtual circular shapes comprising axes in a predetermined angle in relation to each other.

11. The method according to claim 1, wherein each circular shape has an axis which is 90° in relation to the surface of the circular shape.

12. The method according to claim 1, wherein the area of the placed circular shapes includes a surrounding area for letting an adjustment socket be inserted that will comprise the created hollow space in the rig.

13. The method according to claim 1, comprising virtually placing at least three circular shapes in a row or other symmetry wherein at least one circular shape overlaps with at least two other circular shapes.

14. The method according to claim 1, wherein each circular shape has an axis at a point and wherein said axis is 90° in relation to the normal of a tangent in a point on the virtual bone contact surface.

15. The method according to claim 1, wherein creating a virtual model of a rig further comprises creating a simulated bone surface in the 3D view, which mimics a non-damaged bone surface in a healthy patient and using said simulated bone surface as a base when creating the virtual model of said rig.

16. A method for placement of an implant in a bone and/or cartilage area in a joint comprising placing positioning surface of the rig designed and made according to claim 1 within a joint; and guiding cutting and drilling of cartilage and/or bone through hollow tubular shell of the rig.

17. A rig comprising a guide body in the form of a hollow tubular shell configured to define at least first and second intersecting cylinders, designed and made by the method comprising:
  identifying a damage area in said joint;
  presenting a 3D view of said identified damage area in a virtual model of the joint;
  generating a 3D model of a virtual rig, wherein the generating comprises virtually placing in said 3D view a shape at least partly covering said damage area in said virtual model of the joint;
  creating, based on the position of the virtually placed shape, a position of said hollow tubular shell of the virtual rig;
  selecting the at least first and second intersecting cylinders of the virtual rig, based on the size and form of the virtually placed shape;
  creating a positioning surface of the virtual rig as a bone and/or cartilage engaging end of said hollow tubular shell and which positioning surface is adapted to follow the surface of the joint surrounding the virtually placed shape when the virtual rig is placed in the virtual model of the joint; and
  making the rig according to the virtual rig,
  wherein said hollow tubular shell of the guide body of the virtual rig is configured to define said at least first and second intersecting cylinders by a bore for each respective cylinder; or
  wherein said hollow tubular shell of the guide body of the virtual rig is configured to define said at least first and second intersecting cylinders by an insert guide having at least one bore for at least one of said cylinders, and wherein said hollow tubular shell of the guide body of the virtual rig and said insert are configured such that the insert is insertable in the hollow tubular shell in at least two different positions to define one of said at least two intersecting cylinders in each position; or wherein each of said first and second intersecting cylinders is provided with a circular cross-sectional profile, and:

wherein said circular cross-sectional profile of said first intersecting cylinder has a diameter being different from a diameter of the circular cross-sectional profile of said second intersecting cylinder, or wherein the circular cross-sectional profile of said first intersecting cylinder has a diameter being equal to a diameter of the circular cross-sectional profile of said second intersecting cylinder.

* * * * *